United States Patent
Pawar et al.

(10) Patent No.: US 10,857,708 B2
(45) Date of Patent: *Dec. 8, 2020

(54) FORMING OF ADDITIVELY MANUFACTURED PRODUCT

(71) Applicant: Smith & Nephew, Inc., Memphis, TN (US)

(72) Inventors: Vivek Pawar, Germantown, TN (US); Mark Morrison, Memphis, TN (US); Carolyn Weaver, Collierville, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/392,032

(22) Filed: Apr. 23, 2019

(65) Prior Publication Data

US 2019/0248052 A1 Aug. 15, 2019

Related U.S. Application Data

(63) Continuation of application No. 15/676,413, filed on Aug. 14, 2017, now Pat. No. 10,279,521.

(Continued)

(51) Int. Cl.
*B29C 45/14* (2006.01)
*B33Y 10/00* (2015.01)
(Continued)

(52) U.S. Cl.
CPC ...... *B29C 45/14795* (2013.01); *A61F 2/0077* (2013.01); *A61F 2/3094* (2013.01); *A61F 2/30771* (2013.01); *A61F 2/34* (2013.01); *A61F 2/3859* (2013.01); *B21J 1/003* (2013.01); *B21J 1/02* (2013.01); *B23K 26/342* (2015.10); *B23P 13/02* (2013.01); *B29C 64/00* (2017.08); *B33Y 10/00* (2014.12); *B33Y 40/00* (2014.12); *B33Y 80/00* (2014.12); *A61F 2/389* (2013.01); *A61F 2/3877* (2013.01); *A61F 2002/009* (2013.01);
(Continued)

(58) Field of Classification Search
CPC ........ B33Y 10/00; B33Y 40/00; B33Y 80/00; B33Y 11/30; B29C 45/14795; A61F 2/30771; A61F 2/3877; A61F 2/389; A61F 2/3859; A61F 2002/3097; A61F 2/0077; B21J 1/003; B29L 2031/7532; Y10T 29/4998; B23P 9/02; B23P 13/02; B23K 26/342
See application file for complete search history.

(56) References Cited

U.S. PATENT DOCUMENTS 4,499,048 A 2/1985 Hanejko
5,236,457 A 8/1993 Devanathan
(Continued)

FOREIGN PATENT DOCUMENTS

WO 2001014602 A2 3/2001
WO 2001014602 A3 5/2001
(Continued)

*Primary Examiner* — Jermie E Cozart

(57) ABSTRACT

An exemplary process includes determining a desired pore size, selecting an initial pore size greater than the target pore size, manufacturing a porous structure with the initial pore size, forging the porous structure to form a forged part having the desired pore size, and forming an orthopedic device from the forged part.

19 Claims, 17 Drawing Sheets

Related U.S. Application Data

(60) Provisional application No. 62/374,611, filed on Aug. 12, 2016.

(51) Int. Cl.

| | |
|---|---|
| *B33Y 40/00* | (2020.01) |
| *B33Y 80/00* | (2015.01) |
| *B23K 26/342* | (2014.01) |
| *B21J 1/00* | (2006.01) |
| *A61F 2/00* | (2006.01) |
| *A61F 2/38* | (2006.01) |
| *A61F 2/30* | (2006.01) |
| *A61F 2/34* | (2006.01) |
| *B21J 1/02* | (2006.01) |
| *B29C 64/00* | (2017.01) |
| *B29K 705/08* | (2006.01) |
| *B29L 31/00* | (2006.01) |
| *B21J 7/00* | (2006.01) |
| *B23P 13/02* | (2006.01) |
| *B23P 9/02* | (2006.01) |

(52) U.S. Cl.
CPC ............ *A61F 2002/30028* (2013.01); *A61F 2002/3092* (2013.01); *A61F 2002/3093* (2013.01); *A61F 2002/3097* (2013.01); *A61F 2002/30967* (2013.01); *A61F 2002/30968* (2013.01); *A61F 2002/30971* (2013.01); *A61F 2002/30985* (2013.01); *B21J 7/00* (2013.01); *B23P 9/02* (2013.01); *B29C 2045/14803* (2013.01); *B29K 2705/08* (2013.01); *B29L 2031/7532* (2013.01); *Y10T 29/4998* (2015.01)

(56) References Cited

U.S. PATENT DOCUMENTS

| | | | |
|---|---|---|---|
| 7,497,876 | B2 | 3/2009 | Tuke et al. |
| 8,506,836 | B2 | 8/2013 | Szuromi et al. |
| 8,888,862 | B2 | 11/2014 | McDonnell et al. |
| 10,279,521 | B1 * | 5/2019 | Pawar ............... B23K 26/342 |
| 2013/0204384 | A1 | 8/2013 | Hensley et al. |
| 2013/0304227 | A1 | 11/2013 | Hawkins |
| 2014/0163717 | A1 | 6/2014 | Das et al. |
| 2014/0172116 | A1 | 6/2014 | Maxson et al. |
| 2015/0045903 | A1 | 2/2015 | Neal |
| 2015/0216668 | A1 | 8/2015 | Smith |
| 2015/0336171 | A1 | 11/2015 | Matejczyk et al. |
| 2016/0074166 | A1 | 3/2016 | Coale et al. |

FOREIGN PATENT DOCUMENTS

| | | |
|---|---|---|
| WO | 2005009489 A2 | 2/2005 |
| WO | 2005009489 A9 | 6/2005 |
| WO | 2005009489 A3 | 8/2005 |
| WO | 2015006447 A1 | 1/2015 |
| WO | 2015012911 A2 | 1/2015 |
| WO | 2015/144129 A1 | 10/2015 |

* cited by examiner

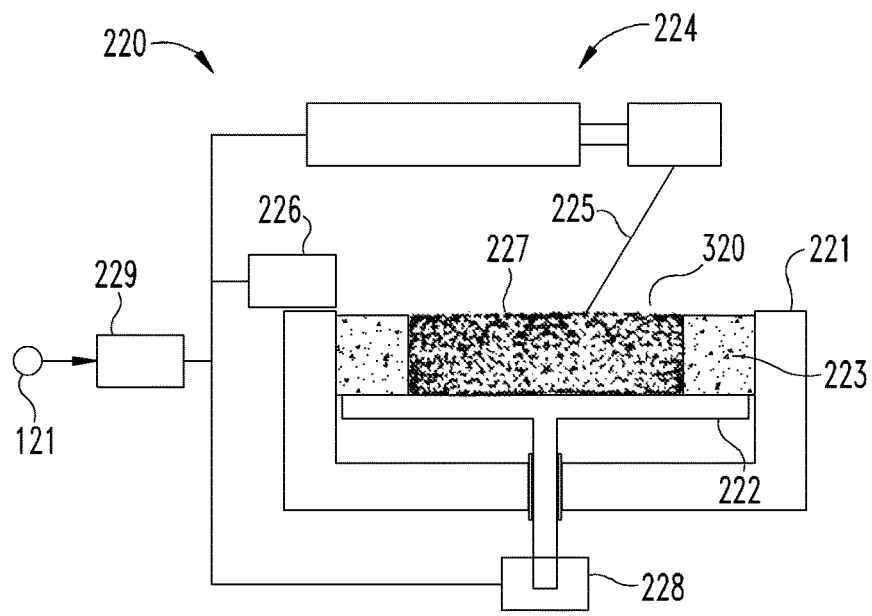
Fig. 4
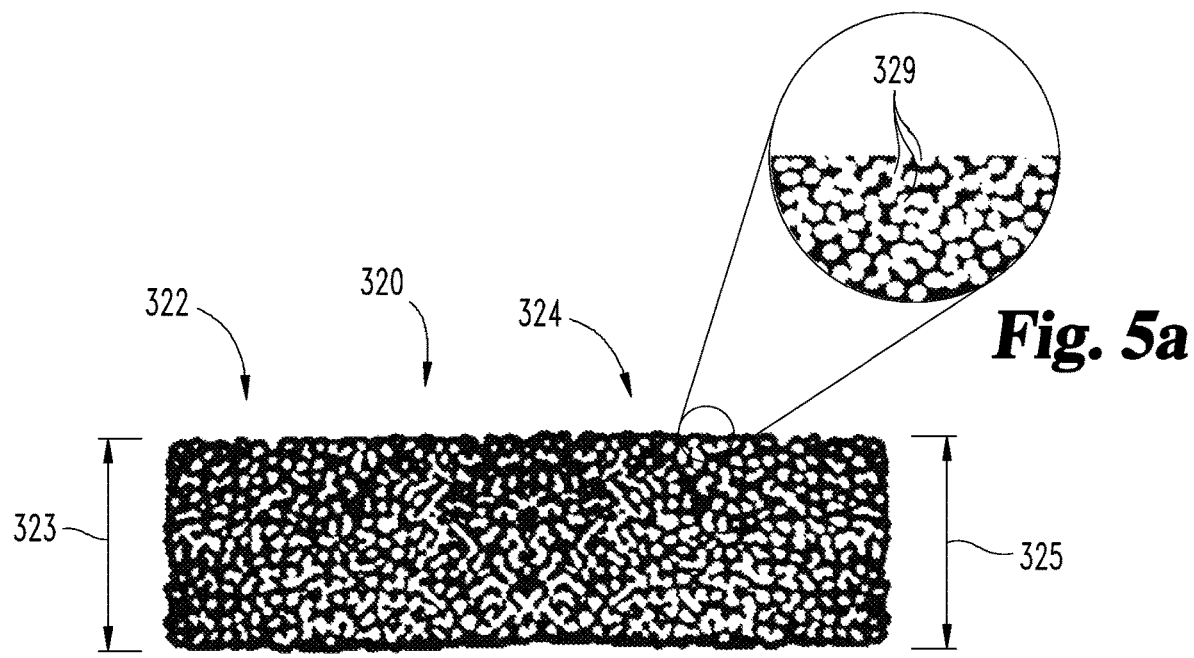
Fig. 5
Fig. 5a

Fig. 8a Fig. 8b

FORMING OF ADDITIVELY MANUFACTURED PRODUCT

CROSS-REFERENCE TO RELATED APPLICATIONS

The present application is a continuation of U.S. patent application Ser. No. 15/676,413 filed Aug. 14, 2017, which claims the benefit of U.S. Provisional Patent Application No. 62/374,611, filed on Aug. 12, 2016, the contents of each application hereby incorporated by reference in their entirety.

TECHNICAL FIELD

The present disclosure generally relates to porous structures, and more particularly but not exclusively relates to methods of making such porous structures using both additive manufacturing techniques and mechanical forming techniques, such as forging and/or rolling.

BACKGROUND

Additive manufacturing techniques are increasingly being used to produce medical devices, as such techniques typically enable the production of components having both porous portions (e.g., in regions where tissue in-growth is desired) and solid portions (e.g., in regions where greater structural strength is needed). Although additive manufacturing has significant advantages, such as enabling the porous sections to be manufactured with porosities and pore sizes tailored to a particular application, these techniques are not without their challenges. For example, while laser additive manufacturing techniques can typically produce much finer pores as compared to electron beam techniques, both approaches generally have difficulty in producing interconnecting pores that are smaller than a threshold size. This threshold size partially depends upon the size of the powder used as a raw material (typically in the range of 40 microns to 100 microns), and partially depends upon the size of the melt pool generated by the beam (typically in the range of 25 microns to 100 microns, depending on beam power, spot size, and scan speed).

In addition, smaller pores may trap fine powder which can be difficult to remove during the cleaning process. Although these smaller pores may be unsuitable for tissue in-growth, they may be suitable to partially infiltrate polymeric compositions to produce components for musculoskeletal articulating and non-articulating surfaces. When polymeric compositions are infiltrated in larger pores, there is a risk of the polymeric composition infiltrating through the entire thickness of the porous part, thereby clogging the pores that are typically provided to promote tissue in-growth. Another challenge associated with additive manufacturing is the time it takes to produce the porous components, as the computing and printing time can be significantly larger for structures with smaller pores than for those with larger pores.

Certain existing approaches have attempted to overcome these challenges by tailoring parameters of the additive manufacturing process itself. For example, certain approaches to preventing undesired infiltration of polymeric compositions include providing a thicker cross-section of the metallic portions of the manufactured product, or creating a gradient in the pore sizes. However, these approaches can produce additional challenges, such as those associated with providing tissue-conserving devices where minimal amount of metal and polyethylene is required, or where a thicker cross-section of polyethylene is required. One current approach to reducing the printing time is to increase the beam power and scan speed, such that a thicker layer is built on each pass. However, this approach comes with the challenge of increasing the size of the melt pool, and thus may further reduce the ability to produce finer pores. For these reasons among others, a need remains for further improvements in this technological field.

SUMMARY

An exemplary process includes determining a desired pore size, selecting an initial pore size greater than the target pore size, manufacturing a porous structure with the initial pore size, forging the porous structure to form a forged part having the desired pore size, and forming an orthopedic device from the forged part. Further embodiments, forms, features, and aspects of the present application shall become apparent from the description and figures provided herewith.

BRIEF DESCRIPTION OF THE FIGURES

FIG. 4 is a schematic representation of an additive manufacturing device that may be included in the system illustrated in FIG. 2.

FIG. 5 illustrates an embodiment of a porous structure formed using the additive manufacturing device illustrated in FIG. 4; the inset of FIG. 5a is an enlarged view of a portion of the porous structure.

DETAILED DESCRIPTION OF ILLUSTRATIVE EMBODIMENTS

Figure 1A:
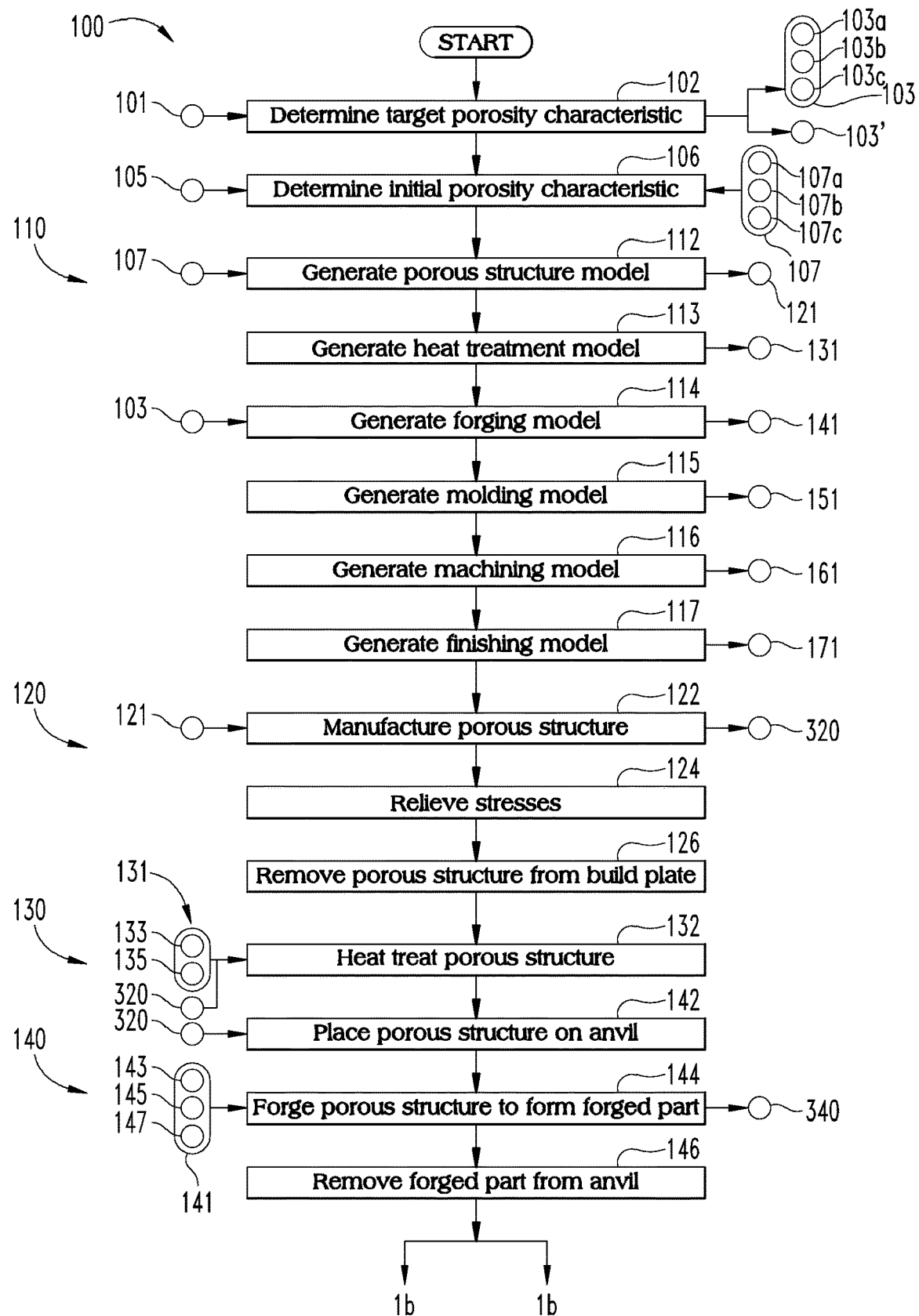
FIG. 1 is a schematic flow diagram of a process according to certain embodiments; the flow diagram is split into two portions, designated FIGS. 1a and 1b.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. It should further be appreciated that although reference to a "preferred" component or feature may indicate the desirability of a particular component or feature with respect to an embodiment, the disclosure is not so limiting with respect to other embodiments, which may omit such a component or feature. Further, when a particular feature, structure, or characteristic is described in connection with an embodiment, it is submitted that it is within the knowledge of one skilled in the art to implement such feature, structure, or characteristic in connection with other embodiments whether or not explicitly described.

Additionally, it should be appreciated that items included in a list in the form of "at least one of A, B, and C" can mean (A); (B); (C); (A and B); (B and C); (A and C); or (A, B, and C). Similarly, items listed in the form of "at least one of A, B, or C" can mean (A); (B); (C); (A and B); (B and C); (A and C); or (A, B, and C). Further, with respect to the claims, the use of words and phrases such as "a," "an," "at least one," and/or "at least one portion" should not be interpreted so as to be limiting to only one such element unless specifically stated to the contrary, and the use of phrases such as "at least a portion" and/or "a portion" should be interpreted as encompassing both embodiments including only a portion of such element and embodiments including the entirety of such element unless specifically stated to the contrary.

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures unless indicated to the contrary. Additionally, the inclusion of a structural or method feature in a particular figure is not meant to imply that such feature is required in all embodiments and, in some embodiments, may be omitted or may be combined with other features.

Figure 1B:
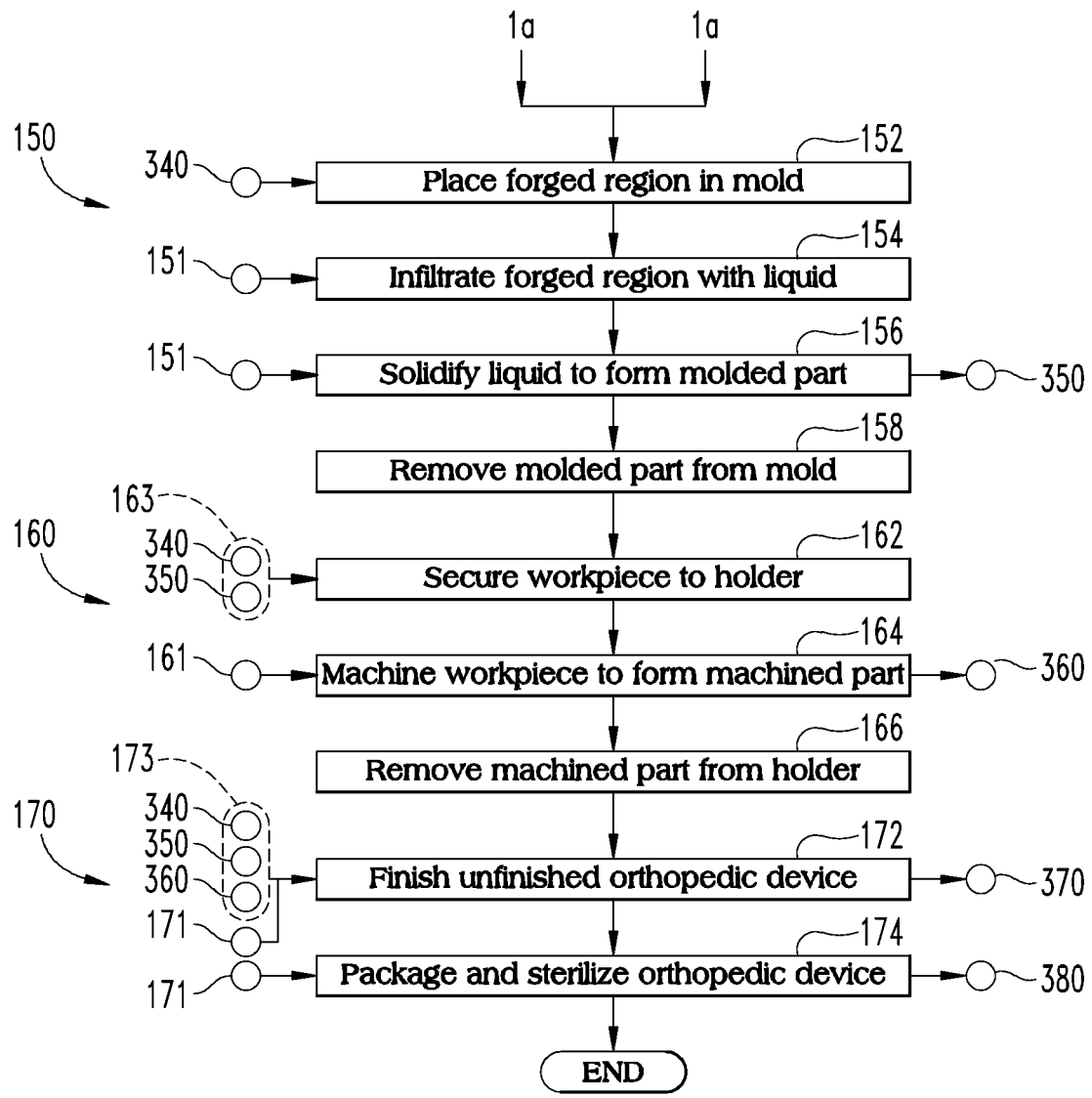
Figure 2:
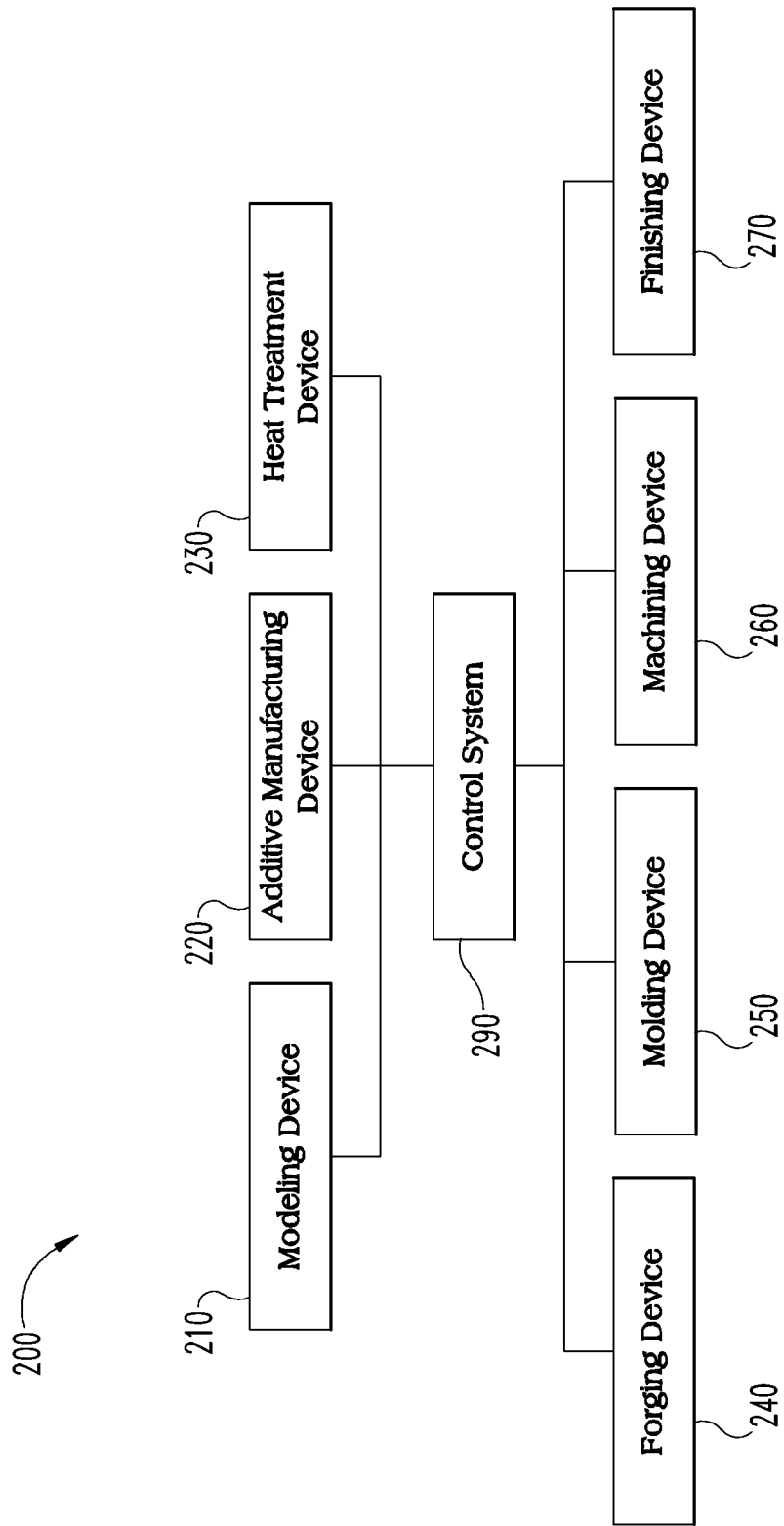
FIG. 2 is a schematic block diagram of a system that may be utilized in connection with the process illustrated in FIG. 1.

With reference to FIGS. 1-13, illustrated therein are a process 100 and a system 200 which may be utilized to manufacture a product, generally indicated with 300-series reference characters. More specifically, FIG. 1 is a schematic flow diagram of a process 100 according to certain embodiments, FIG. 2 is a schematic block diagram of a system 200 according to certain embodiments, and FIGS. 3-13 illustrate various components of the system 200 and stages of the product progressing from a unit cell 310 (FIG. 3) to a finished orthopedic device 370 (FIG. 13). Operations illustrated for the processes in the present application are understood to be examples only, and operations may be combined or divided, and added or removed, as well as re-ordered in whole or in part, unless explicitly stated to the contrary. Unless specified to the contrary, it is contemplated that certain operations or steps performed in the process 100 may be performed wholly by one of the devices illustrated in connection with the system 200, or that the operations or steps may be distributed among one or more of the devices and/or additional devices or systems which are not specifically illustrated in FIGS. 2-12.

The illustrated form of the process 100 generally includes a modeling procedure 110, an additive manufacturing procedure 120, a heat treatment procedure 130, a forging procedure 140, a molding procedure 150, a machining procedure 160, and a finishing procedure 170, one or more of which may be omitted in certain embodiments. Additionally, the illustrated system 200 generally includes a modeling device 210, an additive manufacturing device 220, a heat treatment device 230, a deforming device in the form of a forging device 240, a molding device 250, a machining device 260, and a finishing device 270, each of which may be utilized in connection with a corresponding one of the procedures 110-170. As will be appreciated, one or more of the devices 210-270 may be omitted from the system 200, for example in embodiments in which the corresponding one of the procedures 110-170 is omitted from the process 100. The system 200 may further include a control system 290 or network, which may be in connected with one or more of the devices 210-270 to control the devices and/or provide communication between the devices.

Figure 7:
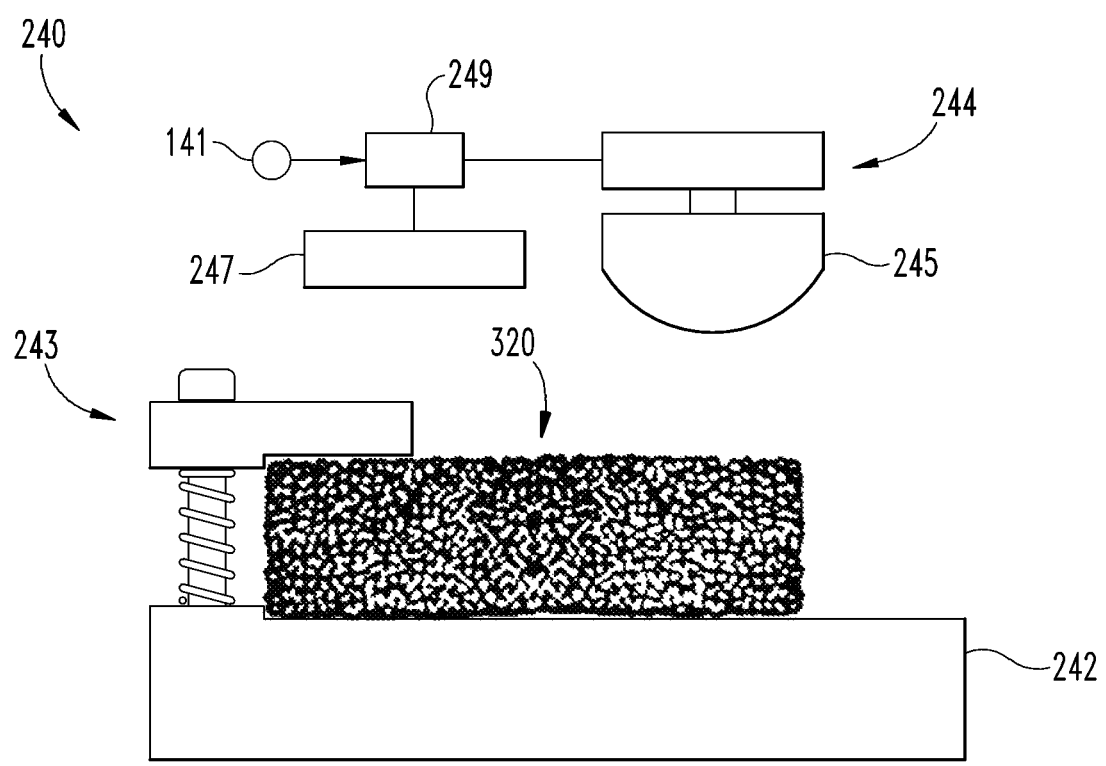
FIG. 7 is a schematic representation of a forging device that may be included in the system illustrated in FIG. 2.
Figure 8:
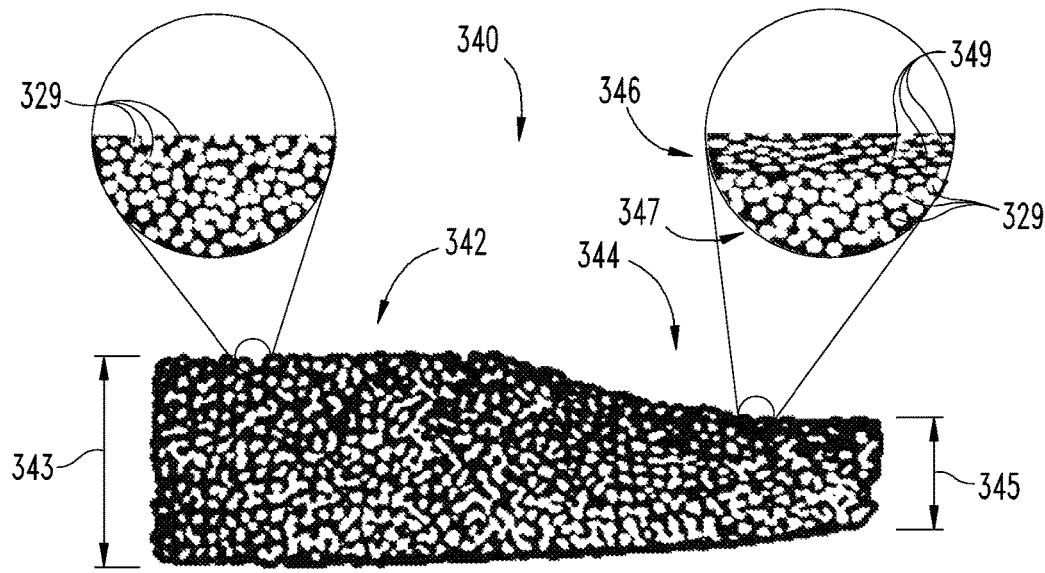
FIG. 8 illustrates an embodiment of a forged part, which is formed from the porous structure illustrated in FIG. 5; the insets of FIGS. 8a and 8b are enlarged views of portions of the forged part.
Figure 9:
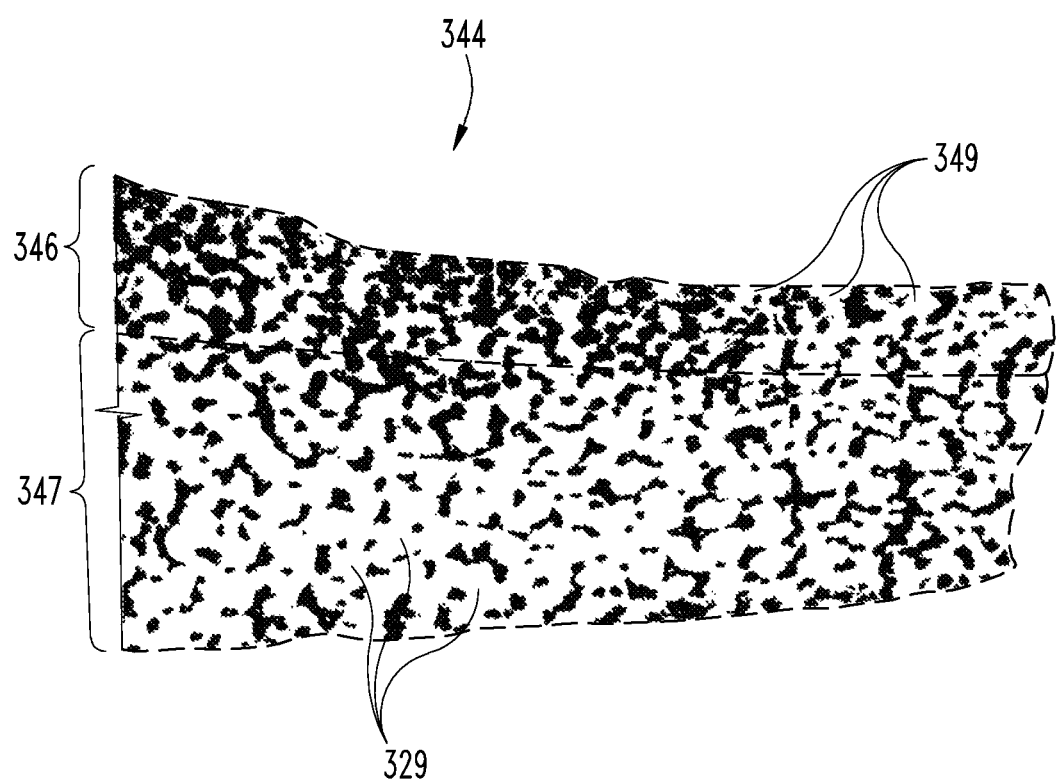
FIG. 9 is a cross-sectional illustration of a portion of the forged part illustrated in FIG. 8.

As described in further detail below, the modeling procedure 110 involves generating one or more models using the modeling device 210, and the additive manufacturing procedure 120 involves utilizing the additive manufacturing device 220 to manufacture a porous structure 320, which includes at least one porous portion 324 having a plurality of original or initial pores 329 (FIGS. 4 and 5). The heat treatment procedure 130 generally involves heat treating the porous structure 320 with the heat treatment device 230 (FIG. 6), and the forging procedure 140 involves utilizing the forging device 240 on the porous structure 320 to form a forged part 340, which includes a deformed layer 346 having modified pores 349 and a second layer 347 (FIGS. 7-9). The molding procedure 150 involves utilizing the molding device 250 to form a molded part 350 including the forged part 340 and an attached part 355 (FIGS. 10 and 11), and the machining procedure 160 involves utilizing the machining device 260 to form a machined part 360 from a workpiece 163 (FIG. 12), such as the forged part 340 or the molded part 350. Additionally, the finishing procedure 170 involves utilizing the finishing device 270 to form a finished orthopedic device 370 from an unfinished orthopedic device 173, such as the forged part 340, molded part 350, or machined part 360.

Figure 13A:
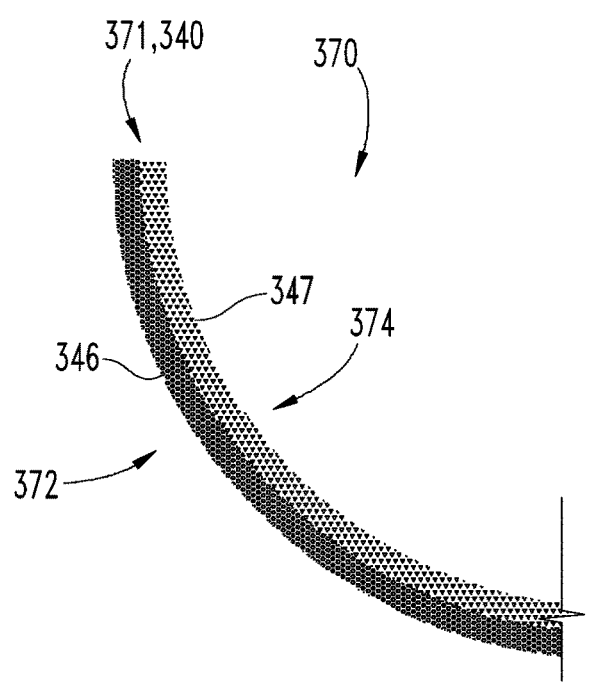
FIGS. 13a and 13b are schematic representations of orthopedic devices that may be formed using the process illustrated in FIG. 1.
Figure 13B:
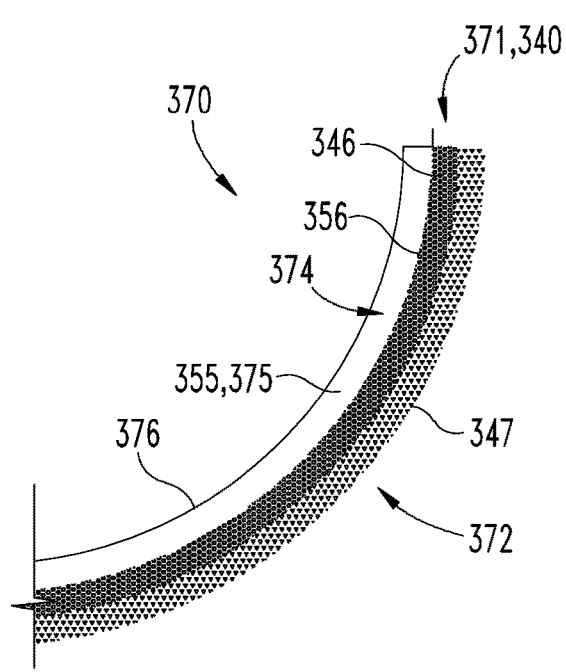

With specific reference to FIGS. 13a and 13b, the orthopedic device 370 includes a body portion 371 having a tissue-facing region 372 and an opposite second region 374. More specifically, the body portion 371 is formed of the forged part 340, and each of the body portion regions 372, 374 is formed of one of the forged part layers 346, 347. In certain forms (FIG. 13a), the tissue-facing region 372 may be formed of the deformed layer 346, and the second region 374 may be formed of the second layer 347. In other forms (FIG. 13b), the second region 374 may be formed of the deformed layer 346, and the tissue-facing region 372 may be formed of the second layer 347. In such embodiments, the device 370 may further include a polymeric portion 375, which is formed of the attached part 355 and has a smooth surface 376. In certain embodiments, the polymeric portion 375 may be an articular portion, and the smooth surface 376 may be an articular surface. In other embodiments, the smooth surface 376 may not necessarily be an articular surface, and may instead be configured to discourage attachment of soft tissue to the polymeric portion 375. By way of example, an orthopedic device 370 including the polymeric portion 375 may be provided in the form of a resurfacing acetabular or tibial device.

The process 100 may begin with an operation 102, which generally includes determining or selecting a target porosity characteristic 103 based upon at least one criterion 101. More specifically, the operation 102 includes determining the target porosity characteristic 103 for the deformed layer 346 of the forged part 340, and the criteria 101 may relate to a desired performance characteristic for the deformed layer 346. As noted above, the deformed layer 346 of the forged part 340 corresponds to one of the regions 372, 374 of the orthopedic device 370. Accordingly, the operation 102 may alternatively be considered to involve determining the target porosity characteristic 103 for the corresponding one of the regions 372, 374. The target porosity characteristic 103 may, for example, include one or more of a target average pore size 103a, a target range 103b of pore sizes, and a target porosity fraction 103c for the deformed layer 346. In certain embodiments, the target pore size range 103b may be related to the target average pore size 103a, or the average pore size 103a may be defined as the average of the target range 103b.

In certain embodiments, the criteria 101 may include a tissue in-growth criterion, and the target porosity characteristic 103 may be selected to promote tissue in-growth in the porous region 374. For example, a target porosity characteristic 103 based upon such a criterion may include a target average pore size 103a of less than 1000 microns and/or a porosity fraction 103c in the range of 35% to 70%. The target porosity characteristic 103 may additionally or alternatively include a target range 103b of pore sizes. For example, such a range 103b may have a lower limit between 50 microns and 300 microns and/or an upper limit between 500 microns and 1000 microns.

In certain embodiments, one or more of the criteria 101 may relate to infiltration of a polymeric composition, and the target porosity characteristic 103 may be selected to provide a desired level of infiltration during the molding procedure 150, or a desired degree of control over such infiltration. For example, a target porosity characteristic 103 based upon such a criterion 101 may include a target average pore size 103a of less than 500 microns and/or a porosity fraction 103c in the range of 15% to 35%.

In certain embodiments, the operation 102 may further include determining at least one additional target porosity characteristic 103', such as for a second porous region of the orthopedic device 370. Further details regarding exemplary selections for the target porosity characteristics 103, 103' are provided below.

The process 100 also includes an operation 106, which includes selecting an initial porosity characteristic 107 for at least one porous portion 324 of the porous structure 320 based upon at least one criterion 105. As described in further detail below, the forging procedure 140 generally involves deforming at least one portion 324 of the porous structure 320 to form a forged region 344 including a deformed layer 346. As a result of the forging, the deformed layer 346 has a smaller average pore size and a lower porosity than the corresponding portion 324 of the initial part 320. Accordingly, one of the criteria 105 may relate to the target porosity characteristic 103, and the operation 106 may include selecting an initial porosity characteristic 107 greater than the target porosity characteristic 103. For example, the operation 106 may include selecting one or more of an initial average pore size 107a greater than the target average pore size 103a, an initial pore size range 107b higher than the target pore size range 103b, and an initial porosity fraction 107c greater than the target porosity fraction 103c. As described in further detail below, selection of the initial porosity characteristic 107 may affect and be affected by the operating parameters associated with the additive manufacturing procedure 120. Accordingly, one or more of the criteria 105 may relate to the additive manufacturing procedure 120 and/or the additive manufacturing device 220.

Figure 3:
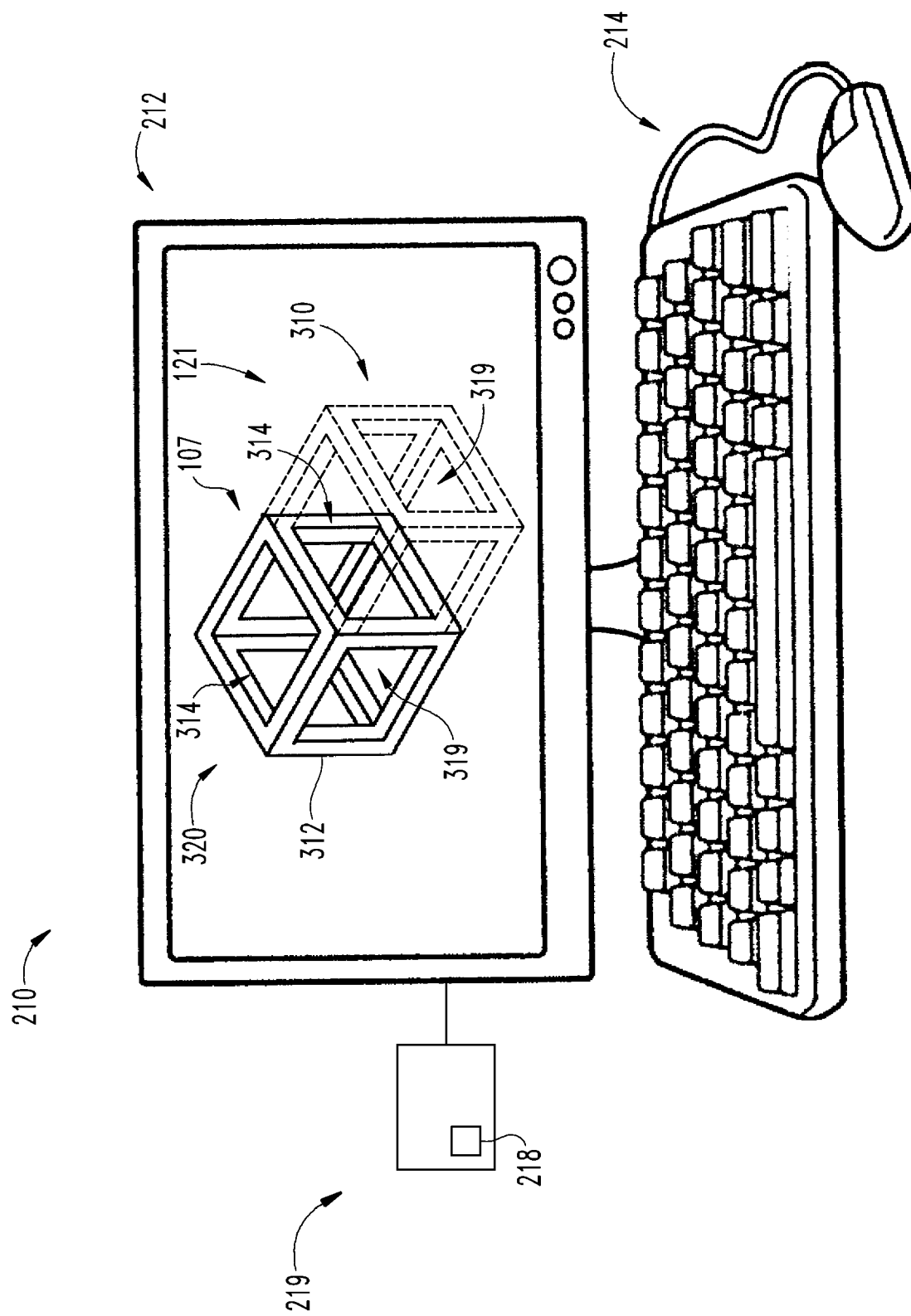
FIG. 3 is a schematic representation of a modeling device that may be included in the system illustrated in FIG. 2

With additional reference to FIG. 3, the process 100 may include a modeling procedure 110, which generally involves generating one or more models using the modeling device 210. The illustrated modeling device 210 includes a display device 212, a user input device 214, and a computing device 219 operably connected with the display device 212 and the user input device 214. The computing device 219 includes modeling tools 218, which enable the user to generate the models, view information relating to the models on the display device 212, and manipulate the models using the user input device 214. Further details regarding an exemplary form of the computing device 219 is provided below with reference to FIG. 17.

The modeling procedure 110 includes an operation 112, which involves generating a porous structure model 121 having the initial porosity characteristic 107. The operation 112 may, for example, include generating a unit cell 310 including a plurality of struts 312, which generally define a plurality of faces 314 and a pore 319 of the unit cell 310. While the unit cell 310 is illustrated as a cubical unit cell, it is also contemplated that the unit cell 310 may be provided in another form of space-filling polyhedron, such as an icosahedron or a dodecahedron. The operation 112 may include selecting a size for unit cell 310 and one or more thicknesses for the struts 312 based upon the initial porosity characteristic 107. The operation 112 may further include generating the porous structure model 121 by instancing the unit cell 310 to create a lattice in which adjacent cells share a face 314 and the pores 319 are interconnected. As will be appreciated, the degree of interconnection between pores of adjacent unit cells depends upon a number of factors, such as the size of the pores 319 and the thickness of the struts 312.

In the illustrated form, the porous structure model 121 is defined by a regular lattice comprising a plurality of identical unit cells 310, such that the pore 319 of each cell 310 has a pore size corresponding to the initial pore size 107a, and the ratio of the total volume of the pores 319 to the total volume of the model 121 corresponds to the porosity fraction 107c. It is also contemplated that unit cells 310 may be tessellated in another manner and/or at least partially or fully randomized to form the model, and that the cells vary in size and/or geometry. For example, the size of the pores 319 may vary within the target range 107b, such that the model 121 has the initial average pore size 107a and the initial porosity fraction 107c. In certain embodiments, the operation 112 may involve generating the model 121 such that when a porous structure built according to the model 121 is subjected to the forging procedure 140, the resulting deformed layer 346 has the target porosity characteristic 103.

The procedure 110 may further include one or more additional operations 113-117, each of which may involve generating an additional model to be utilized in a corresponding one of the procedures 130-170. For example, an operation 113 may involve generating a heat treatment model 131 to be utilized in the heat treatment procedure 130, an operation 114 may involve generating a forging model 141 to be utilized in the forging procedure 140, and an operation 115 may involve generating a molding model 151 to be utilized in the molding procedure 150. Similarly, an operation 116 may involve generating a machining model 161 to be utilized in the machining procedure 160, and an operation 117 may involve generating a finishing model 171 to be utilized in the finishing procedure 170. In certain embodiments, one or more of the models may have been previously generated or may be unnecessary, and the corresponding operations may be omitted accordingly.

With additional reference to FIGS. 4 and 5, the additive manufacturing procedure 120 generally involves manufacturing a porous structure or initial part 320 using the additive manufacturing device 220. In the illustrated form, the additive manufacturing device 220 generally includes a housing 221, a build plate 222 movably mounted to the housing 221, a bed of raw material 223 supported by the build plate 222, a beam scanner 224 operable to generate a beam 225, and a controller 229 in communication with the beam scanner 224. The controller 229 may further be in communication with an actuator 228 operable to move the build plate 222 and/or a material distributor 226 operable to distribute raw material 223. In certain embodiments, the controller 229 may be in communication with the network and/or controlled by the control system 290.

In certain forms, the additive manufacturing procedure 120 may be provided as a selective laser sintering (SLS) procedure, in which the beam 225 is provided in the form of a laser and the raw material 223 is provided in a powdered form. By way of example, the powdered raw material 223 may include stainless steel and/or one or more alloys, such as titanium alloys, zirconium alloys, and cobalt-chromium alloys. In other embodiments, other forms of additive manufacturing techniques may be utilized in the additive manufacturing procedure 120, such as those in which the beam 225 is provided in the form of an electron beam and/or the raw material 223 is provided as a liquid.

The additive manufacturing procedure 120 includes an operation 122, which includes receiving the porous structure model 121 at the additive manufacturing device 220, and building the porous structure 320 according to the model 121. During the operation 122, the beam scanner 224 generates a beam 225 which causes portions of the raw material 223 contacted by the beam 225 to transition states, thereby forming an added material layer 227 to the part 320. In the illustrated form, the raw material 223 that is melted by the beam 225 to generate a melt pool, which solidifies to form a portion of the added material layer 227. The controller 229 may control the generation and direction of the beam 225 such that the added material layer 227 is formed according to a corresponding layer in the model 121.

After each added material layer 227 is formed on the part 320, the build plate 222 is lowered by a distance corresponding to the thickness of the added material layer 227. For example, the controller 229 may operate an actuator 228 such as a motor or hydraulic device to lower the build plate 222 by the appropriate amount. With the build plate 222 lowered, the recently added layer 227 is covered by raw material 223. For example, the controller 229 may issue a command which causes the material distributor 226 to distribute additional raw material 223 over the previously-added material layer 227. The steps are then repeated to form additional added material layers 227 according to the model 121 until the porous structure 320 is complete.

The procedure 120 may further include an operation 124, which involves relieving the initial part 320 of stresses generated during the building operation 122. The operation 124 may, for example, include utilizing a stress-relief annealing technique while the part 320 is still mounted to the build plate 222. The procedure 120 further includes an operation 126, which involves removing the part 320 from the build plate 222. The operation 126 may further include cleaning the part 320 to remove excess raw material 223 from the part 320, for example using conventional wet and/or dry cleaning techniques.

As illustrated in FIG. 5, the initial part 320 includes at least one porous portion 322, 324 having a plurality of original or initial pores 329. At least one of the porous portions 322, 324 has the initial porosity characteristic 107 selected in the operation 106. For example, the initial porosity characteristic 107 may include an initial average pore size 107a, and the pores 329 in at least one of the porous portions 322, 324 may have an average pore size corresponding to the initial average pore size 107a. In certain embodiments, the initial porosity characteristic 107 may include a range 107b of initial pore sizes, and the pores 329 may have sizes defined by the range 107b. Additionally or alternatively, the initial porosity characteristic 107 may include an initial porosity fraction 107c, and the pores 329 may provide at least one of the portions 322, 324 with the selected initial porosity fraction 107c. As illustrated in the inset of FIG. 5a, the initial pores 329 exhibit a relatively high level of interconnection with one another.

As noted above, selection of the initial porosity characteristic 107 may affect and be affected by the operating parameters associated with the additive manufacturing procedure 120. For example, laser-based additive manufacturing techniques can typically produce much finer pores compared to those techniques which utilize an electron beam. However, both techniques have difficulty in producing interconnecting pores that are smaller than a threshold pore size. The threshold pore size depends on the operating parameters associated with the particular additive manufacturing technique being utilized, such as the powder size of the raw material 223 and the size of the melt pool generated by the beam 225. For example, the powder size may be in the range of 40 microns to 100 microns, and the melt pool diameter may be in the range of 25 microns to 100 microns, depending on beam power, spot size, and scan speed. In such forms, it may be challenging to create initial pores 329 having a size less than a threshold pore size of about 100 microns.

Additionally, the computing and printing time can be significantly larger for structures with smaller pores than those with larger pores. In certain embodiments, the operation 106 may include selecting the initial porosity characteristic 107 based at least in part upon criteria 105 relating to the particular techniques and/or operating parameters to be utilized in the additive manufacturing procedure 120. For example, such criteria 105 may relate to one or more of the average powder size for the raw material 223, the type of beam 225 utilized, the diameter of the melt pool generated by the beam 225, the computing time needed to generate the model 121, and the printing time needed to build the porous structure 320. Additionally or alternatively, a criterion 105 may relate to a threshold pore size, which may be based at least in part upon the powder size associated with the raw material 223 and/or the size of the melt pool generated by the beam 225.

Figure 6:
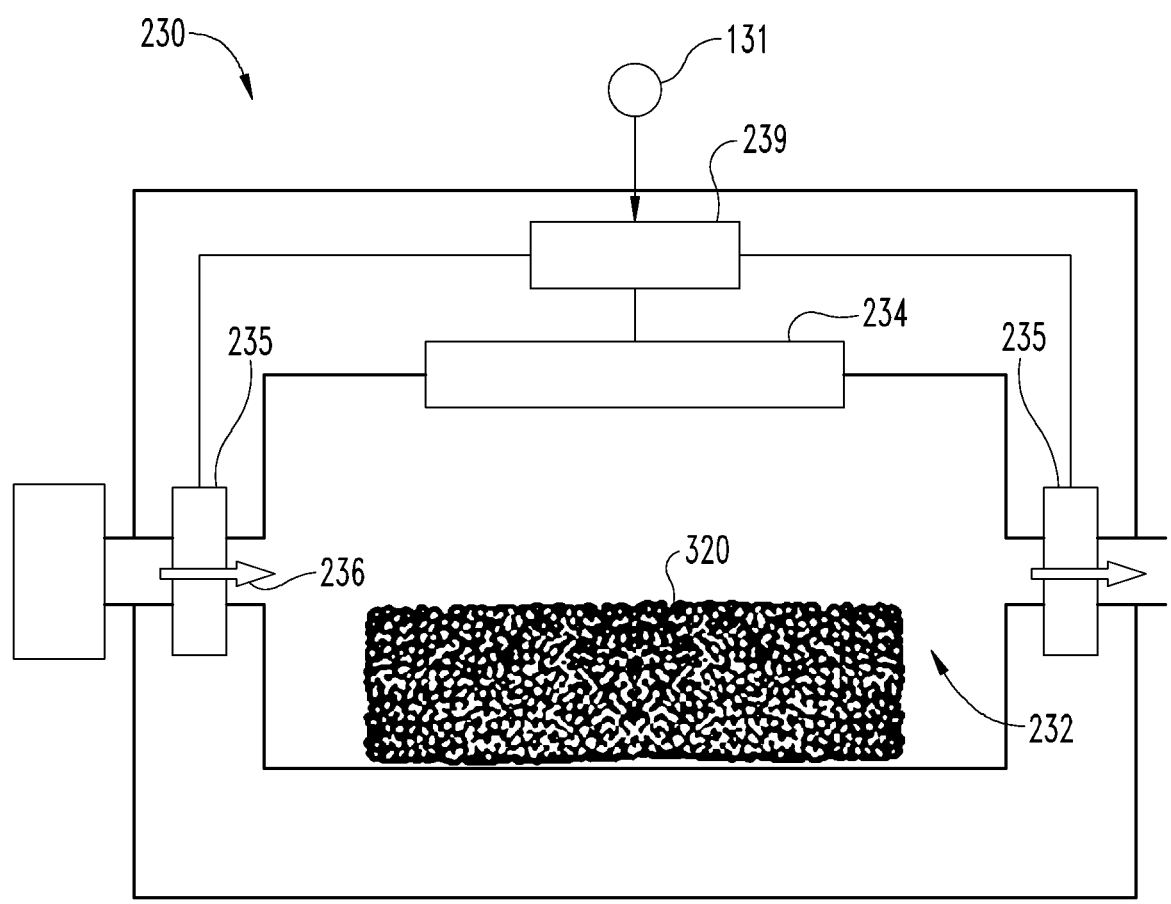
FIG. 6 is a schematic representation of a heat treatment device that may be included in the system illustrated in FIG. 2.

With additional reference to FIG. 6, the process 100 may further include the heat treatment procedure 130, which generally involves utilizing the heat treatment device 230 to heat treat the porous structure 320. In the illustrated form, the heat treatment device 230 is provided in the form of an oven or high-temperature furnace 230 having a chamber 232 operable to receive the initial part 320, a heating element 234 operable to heat the part 320, and a controller 239 in communication with the heating element 234. The oven 230 may further include one or more pumps 235 configured to control the flow of a gas 236 or vacuum pressure into and/or out of the chamber 232, and the controller 239 may be in communication with the pumps 235.

The heat treatment procedure 130 includes an operation 132, which includes receiving the heat treatment model 131 at the heat treatment device 230, and heat treating the porous structure 320 according to the model 131. In certain embodiments, the heat treatment model 131 may include a temperature profile 133 defining one or more of a heating rate, a target temperature, a time associated with the target temperature, and a cooling rate. In such forms, the operation 132 may include controlling the heating element 234 such that the temperature within the chamber 232 increases to the target temperature at the heating rate, maintains the target temperature for the predetermined amount of time, and decreases from the target temperature at the cooling rate. In certain embodiments, the heat treatment model 131 may further include a gas flow model 135, and the operation 132 may include controlling the pumps 235 to control the inflow and/or outflow of the gas 236 according to the gas flow model 135.

With additional reference to FIGS. 7 and 8, the forging procedure 140 generally involves utilizing the forging device 240 to form a forged part 340 from the initial part 320. In the illustrated form, the forging device 240 generally includes an anvil 242 having a securing device 243, a hammer 244 having a striker 245, and a controller 249 in communication with the hammer 244. The forging device 240 may further include a heating element 247, and the controller 249 may be in communication with the heating element 247. The forging procedure 140 includes an operation 142, which generally includes placing the porous structure 320 on the anvil 242, and which may further include securing the porous structure 320 to the anvil 243 using the securing device 243. While the securing device 243 is illustrated as a clamp, it is also contemplated that other forms of securing device may be utilized.

The forging procedure 140 also includes an operation 144, which includes receiving the forging model 141 at the controller 249, and operating the forging device 240 according to the model 141. For example, the forging model 141 may include location information 143 indicating locations at which the part 320 is to be struck, and striking information 145 indicating the number of times the striker 245 is to strike the part 320 at each location and the force with which each strike is to be delivered. In such forms, the operation 144 may include operating the hammer 244 to cause the striker 245 to strike the part 320 according to the striking information 145 in the locations indicated by the location information 143.

In certain embodiments, the forging model 141 may include heating information 147, and the operation 144 may include operating the heating element 247 according to the heating information 147. For example, the operation 144 may include operating the heating element 247 to bring the part 320 to a temperature indicated by the heating information 147 prior to operating the hammer 244 according to the striking information 145. In certain embodiments, the operation 144 may include operating the heating element 247 to maintain the part 320 at the desired temperature for at least a portion of the duration of the forging.

With the operation 144 complete, at least one porous portion 324 of the initial part 320 has been converted to a forged region 344, and the initial part 320 has been converted to a forged part 340. The procedure 140 may then continue to an operation 146, which involves removing the forged part 340 from the anvil 242. In certain embodiments, one or more heat treatments may be performed on the forged part 340, such as sintering and/or hipping.

As a result of the forging procedure 140, at least a portion of the porous structure 320 has been deformed, such that the forged part 340 includes a forged region 344. For example, the forged part 340 illustrated in FIG. 8 includes an unforged first region 342 corresponding to the first porous portion 322, and a forged second region 344 corresponding to the second porous portion 324. Additionally, the unforged first region 342 has a first thickness 343 corresponding to the thickness 323 of the first porous portion 322, and the forged second region 344 has a second thickness 345 less than the thickness 325 of the second porous portion 324. The thickness 345 of the forged second region 344 may, for example, be in the range of 50% to 80% of the thickness 325 of the second portion 324 of the initial part 320.

Due to the fact that the unforged region 342 has not been struck, the unforged region 342 maintains the general configuration of the corresponding first portion 322 of the initial porous structure 320. As a result, the unforged region 342 includes the original or initial pores 329, and has the initial porosity characteristic 107. In contrast, at least some of the pores in the forged region 344 have been converted to modified pores 349, such that at least a portion of the forged region 344 has the target porosity characteristic 103. More specifically, the forged region 344 includes a deformed layer 346 formed adjacent the surface struck by the striker 245 during the forging procedure 140, and the deformed layer 346 has the target porosity characteristic 103. It is interesting to note that when a solid structure is subjected to forging, deformation typically occurs throughout the thickness of the forged region. However, it has been found that when a porous structure such as the initial part 320 is subjected to forging, the forged region 344 may retain an undeformed layer 347 below the deformed layer 346.

The retention of such an undeformed layer 347 may depend upon a number of factors, such as the porosity of the porous portion 324 and the reduction in thickness imparted by the forging procedure 140. Thus, layers having varying porosity characteristics can be formed from a uniform porous structure, for example by appropriately selecting the initial porosity characteristic 107 and the forging model 141. Unexpectedly, it has been found that the process of forging a porous structure in this manner may be more easily and efficiently tailored to provide desired porosity characteristics than would be feasible by simply adjusting the operating parameters associated with the additive manufacturing procedure 120. As one example, the deformed layer 346 may be provided with pores 349 having a smaller size than would normally be feasible to produce using the additive manufacturing procedure 120 alone. For example, when the additive manufacturing procedure 120 has a threshold pore size corresponding to the powder size and/or melt pool diameter, the operation 102 may include selecting the target average pore size 103a less than the threshold pore size, and the operation 106 may include selecting the initial average pore size 107a greater than the threshold pore size.

The deformation of the material in the forged region 344 not only reduces the average size of the modified pores 349, but also reduces the level of interconnection between the modified pores 349. Thus, while the unforged region 342 retains the initial porosity characteristics 107 (i.e., a larger average pore size and/or higher porosity) such that the original pores 329 remain highly interconnected (FIG. 8a), the deformed layer 346 of the forged region 344 has the target porosity characteristics 103 (i.e., a smaller average pore size and/or lower porosity) such that the modified pores 349 are less interconnected (FIGS. 8b and 9). Like the unforged region 342, the undeformed layer 347 also retains the initial porosity characteristics 107, such that the pores 329 thereof remain highly interconnected (FIGS. 8b and 9).

While the layer 347 is described above as an undeformed layer which retains the initial porosity characteristic 107, it is to be understood that the layer 347 may be slightly deformed during the forging procedure 140. Accordingly, the layer 347 may alternatively be provided as a substantially undeformed layer which substantially retains initial porosity characteristic 107. Such a substantially undeformed layer 347 may have an average pore size which is slightly smaller than the initial pore size 107a. By way of example, the forging procedure 140 may impart a reduction in average pore size in the range of 10% to 20%, such that the average pore size of the substantially undeformed layer is 80% to 90% of the initial pore size. For purposes of illustration, FIG. 9 illustrates the deformed and undeformed layers 346, 347 as discrete and adjacent layers having the target and initial porosity characteristics 103, 107, respectively. It is to be understood, however, that there may be a gradient in the porosity characteristic, and that a transitional layer may be formed between the deformed layer 346 and the undeformed layer 347.

In the illustrated form, only the second portion 324 of the initial part 320 has been subjected to forging in the forging procedure 140, such that the first region 342 of the forged part 340 is an unforged region. It is also contemplated that the first portion 322 of the initial part 320 may be subjected to forging, such that the first region 342 of the forged part 340 is also a forged region. In certain embodiments, both the first and second portions 322, 324 of the initial part 320 may be forged according to the same striking information 145, such that the first and second regions 342, 344 of the forged part 340 are substantially similar. In other embodiments, the forging model 141 may indicate that one portion of the initial part 320 is to be forged to a greater degree than another portion of the part 320, such as by indicating that the first portion 322 is to be struck a fewer number of times and/or with a lower force than the second portion 324. For example, the forging model 141 may be provided such that after the forging procedure 140, the deformed layer 346 of the second region 344 has the target porosity characteristics 103, and the first region 342 includes a deformed layer having the additional target porosity characteristics 103'. In further embodiments, the forging procedure 340 may further include striking the opposite side of the second porous portion 324, thereby forming an additional deformed layer.

While the illustrated forging procedure 140 utilizes an open-die forging technique, it is to be appreciated that additional and/or alternative techniques may be utilized to form the deformed layer 346. By way of example, the forging procedure 140 may additionally or alternatively utilize a closed-die forging technique and/or an alternative technique which produces deformations by a process other than forging. In certain embodiments, such alternative techniques may include rolling and/or deep drawing the initial part 320.

In certain embodiments, the forged part 340 may be utilized as the workpiece 163 which is machined in the machining operation 160, for example in embodiments in which bulk material removal is required to bring the forged part 340 into the general form of an orthopedic device. In other embodiments, the forged part 340 may be utilized as the unfinished orthopedic device 173 which is finished in the finishing procedure 170, for example in embodiments in which the forged part 340 has the general configuration of the orthopedic device 370 and bulk material removal is not necessary. In certain embodiments, the forged part 340 may be bonded to a metallic substrate, such as by using sintering or diffusion bonding processes, and the resulting part may be utilized as the workpiece 163 or unfinished orthopedic device 173. In further embodiments, the resulting part or the forged part 340 alone may be utilized in the molding procedure 150, further details of which will now be provided.

Figure 10:
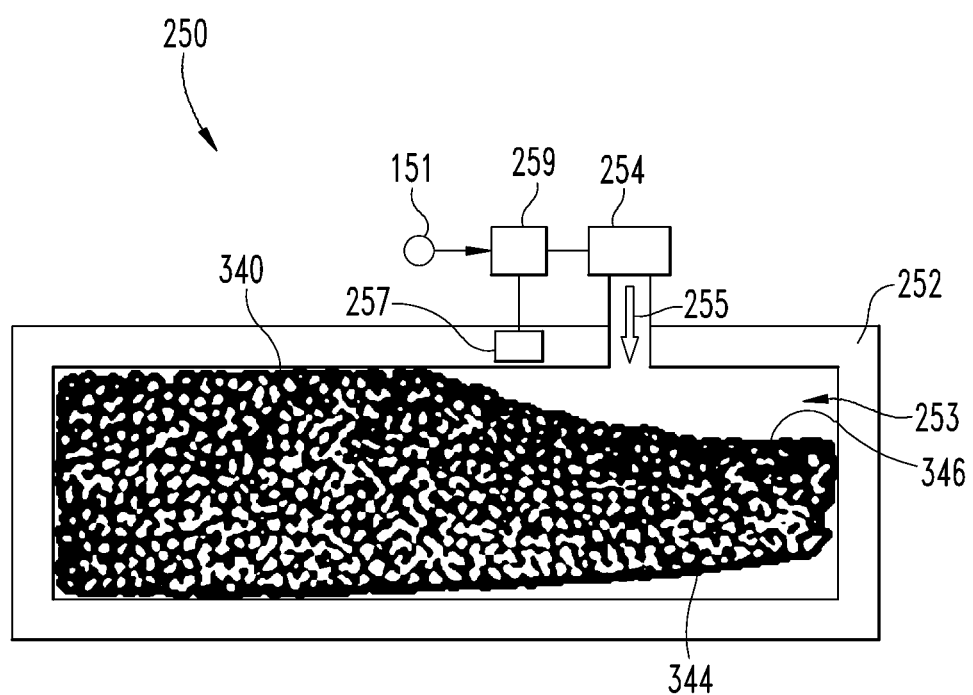
FIG. 10 is a schematic representation of a molding device that may be included in the system illustrated in FIG. 2.
Figure 11:
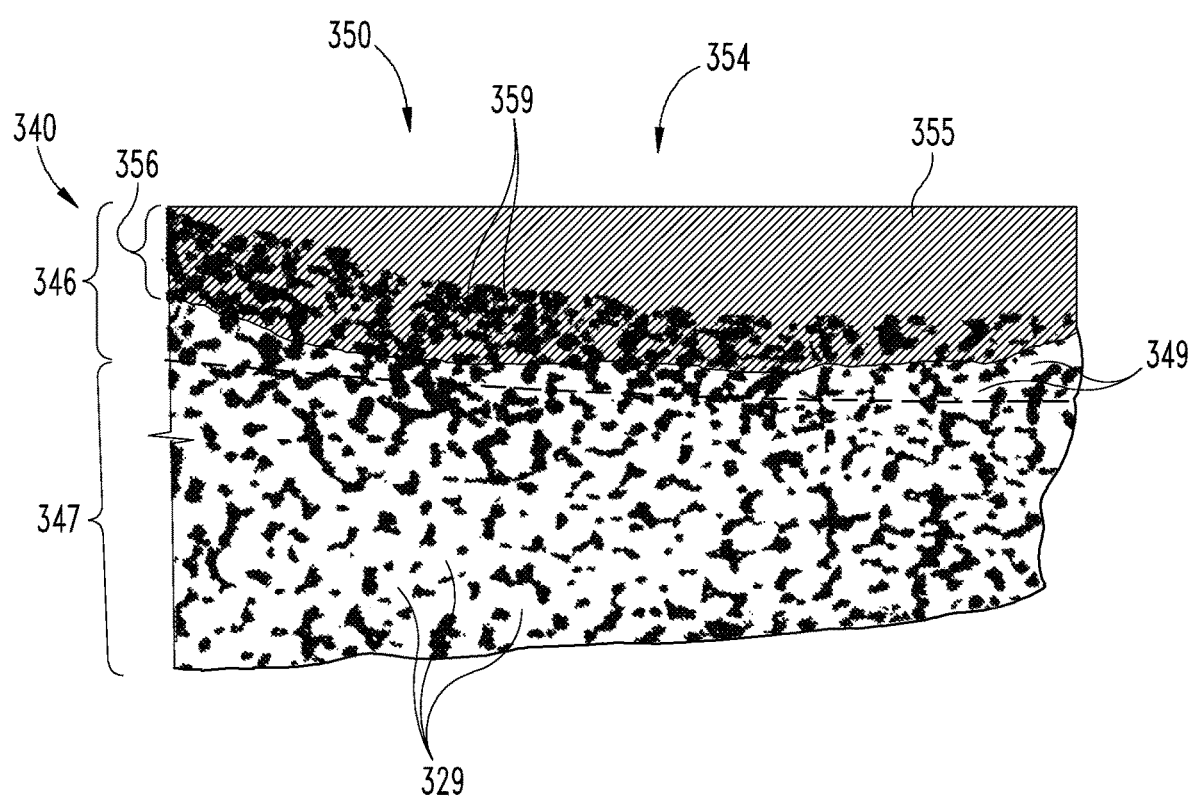
FIG. 11 is a cross-sectional illustration of a portion of a molded part formed from the forged part illustrated in FIGS. 8 and 9.

With additional reference to FIGS. 10 and 11, certain embodiments of the process 100 may include the molding procedure 150, which generally involves utilizing the molding device 250 to form a molded part 350 from the forged part 340. The molding device 250 generally includes a mold 252 having an internal cavity 253, which is configured to provide a polymeric composition 255 received in the mold 252 with a configuration corresponding to a desired geometry of the polymeric portion 375 of the orthopedic device 370. In the illustrated form, the polymeric composition is provided in the form of a liquid 255 stored in a reservoir 256, and the molding device 250 includes an injection device 254 operable to inject the liquid 255 into the cavity 253 under the control of a controller 259. The liquid 255 is one form of a polymeric composition which, when solidified, is suitable to provide an articular or non-articular smooth surface 376 for the orthopedic device 370. By way of example, such a polymeric composition may include a polyethylene compound, such as an ultra-high molecular weight polyethylene or polyether ether ketone (PEEK). The molding device 250 may further include a curing device 257 operable to solidify the liquid 255 or other form of polymeric composition, and the controller 259 may be in communication with the curing device 257. While the illustrated molding device 250 is provided in the form of an injection molding device, it is also contemplated that the molding device 250 may be provided in another form, such as a compression molding device. An example of such a compression molding device 590 is described below with reference to FIG. 15.

The molding procedure 150 includes an operation 152, which generally involves placing at least a portion of the forged part 340 in the mold 252 such that the forged region 344 is received within the cavity 253, and such that the deformed layer 346 faces the cavity 253. The procedure 150 further includes an operation 154, which generally involves infiltrating a polymeric composition into the pores 349 of the deformed layer 346. In the illustrated form, the operation 154 includes injecting the liquid polymeric composition 255 into the cavity 253 such that the liquid polymeric composition 255 infiltrates the deformed layer 347 of the forged region 344. The operation 154 may include receiving the molding model 151 at the controller 259, and operating the injection device 254 to inject the liquid 255 according to the model 151. For example, the molding model 151 may include an injection model 153 indicating the amount of liquid polymeric composition 255 to be injected into the cavity 253 and/or an operating pressure sufficient to result in the desired degree of infiltration.

The molding procedure 150 further includes an operation 156, which generally involves solidifying the liquid polymeric composition 255 to form an attached part 355, such that the molded part 350 includes the forged part 340 and the attached part 355. Due to the fact that at least some of the pores 349 of the deformed layer 346 were infiltrated by the liquid 255 in the operation 154, the operation 156 results in the formation of an infiltrated layer 356 by which the attached part 355 is securely fixed to the forged part 340. More specifically, the infiltrated layer 356 includes infiltrated pores 359 in which portions of attached part 355 are formed, such that the attached part 355 is partially formed within the infiltrated layer 356. While the pores 359 in the infiltrated layer 356 have been filled with the solidified liquid, the size and shape of the pores 359 does not materially change. Accordingly, the deformed layer 346 may be considered to retain the target porosity characteristic 103.

In certain embodiments, the molding model 151 may include a curing model 157, and the operation 156 may include solidifying the liquid polymeric composition 255 by operating the curing device 257 according to the curing model 157. In other embodiments, the operation 156 may not necessarily involve operating the curing device 257, and may instead involve allowing the liquid 255 to solidify by cooling. With the operation 156 complete and the molded part 350 formed, the procedure 150 may continue to an operation 158, which generally involves removing the molded part 350 from the mold 252.

In the illustrated form, the operation 154 includes operating the molding device 250 such that the liquid polymeric composition 255 does not infiltrate the entire depth of the deformed layer 346. Thus, when the liquid 255 is solidified in the operation 156, the infiltrated layer 356 does not extend into the undeformed layer 347 (FIG. 11). Accordingly, the undeformed layer 347 may remain highly porous, which may be desirable to promote tissue in-growth. Due to the fact that the deformed layer 346 has the smaller average pore size and/or lower porosity defined by the target porosity characteristics 103, infiltration of the liquid polymeric composition 255 into the deformed layer 346 in the operation 154 may be more closely controlled than would be feasible if the deformed layer 346 were to have the larger average pore size and/or higher porosity defined by the initial porosity characteristics 107. In other words, the target porosity characteristics 103 provided to the deformed layer 346 may aid in controlling the depth to which the liquid 255 infiltrates the forged region 344.

In certain embodiments, the molded part 350 may be utilized as the unfinished orthopedic device 173 that is finished in the finishing procedure 170. For example, the manufacturing procedure 120 and/or forging procedure 140 may result in the forged part 340 having a geometry suitable for the body portion 371 of the orthopedic device 370, and the molding procedure 150 may result in the attached part 355 being substantially in the form of the articular portion 375 of the orthopedic device 370. In certain forms, the operation 115 may involve generating the molding model 151 based at least in part upon the desired final configuration of the articular portion 375, and the mold cavity 253 may be formed based upon such a molding model 151, such that the attached part 355 defines the articular portion 375. In other embodiments, the molded part 350 may be utilized as the workpiece 163 which is machined in the machining procedure 160, further details of which will now be provided.

Figure 12:
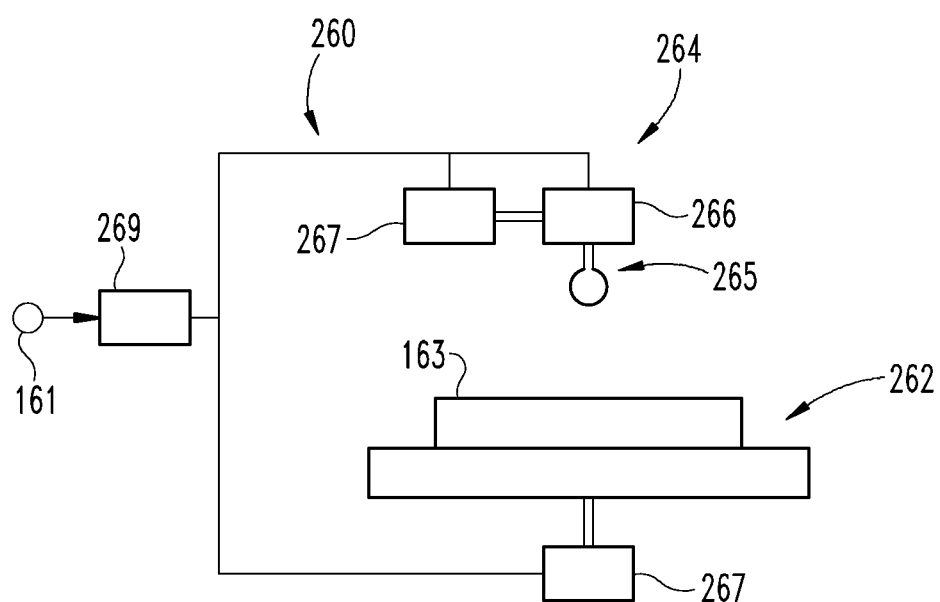
FIG. 12 is a schematic representation of a machining device that may be included in the system illustrated in FIG. 2.

With additional reference to FIG. 12, the process 100 may further include the machining procedure 160, which generally involves utilizing the machining device 260 to form a machined part 360 from a workpiece 163, such as the forged part 340 or the molded part 350. The process 100 may include the machining procedure 160 when bulk material removal is needed to bring the forged part 340 or molded part 350 into the general form desired for the orthopedic device 370. The machining device 260 generally includes a holder 262, a mill 264 including a cutting bit 265, and a controller 269 which controls operation of the mill 264. The machining device 260 may further include at least one driver 267 operable to move the holder 262 and/or the mill 264 in response to commands from the controller 269. For example, the machining device 260 may be a Computer Numerical Control (CNC) machining device, and the controller 269 may control the mill 264 and/or the driver 267 to machine the workpiece 163 according to the machining model 161.

The machining procedure 160 may begin with an operation 162, which generally involves securing the workpiece 163 to the holder 262. The procedure 160 may then continue to an operation 164, which generally involves receiving the machining model 161 at the controller 269, and machining the workpiece 163 according to the model 161. More specifically, the operation 164 includes removing bulk material from the workpiece 163 such that the machined part 360 has the general form desired for the orthopedic device 370. In certain embodiments, the workpiece 163 may include the forged part 340, and the operation 164 may include machining the forged part 340 into a form suitable to serve as the body portion 371 of the orthopedic device 370. In certain embodiments, the workpiece 163 may be provided in the form of the molded part 350, and the operation 164 may include machining the attached part 355 into a form suitable to serve as the articular surface 376 of the orthopedic device 370. With the operation 164 complete, the procedure 160 may continue to an operation 166, which involves removing the machined part 360 from the holder 262. In certain embodiments, the machined part 360 may be utilized as the unfinished orthopedic device 173 that is finished in the finishing operation 170, further details of which will now be provided.

The finishing procedure 170 generally involves utilizing the finishing device 270 to form a finished orthopedic device 370 from an unfinished orthopedic device 173. As noted above, the unfinished orthopedic device 173 may be provided as the forged part 340, the molded part 350, or the machined part 360. For example, in embodiments in which the forged part 340 is substantially in the form of the body 371 of the orthopedic device 370, the bulk material removal provided in the machining procedure 160 may be unnecessary, and the forged part 340 may serve as the unfinished orthopedic device 173. As another example, in embodiments in which the molded part 350 is in the general form of the orthopedic device 370 (e.g., the forged part 340 is substantially in the form of the body 371 and the attached part 355 is substantially in the form of the articular portion 375), the molded part 350 may serve as the unfinished orthopedic device 173. As a further example, in embodiments in which the bulk material removal provided by the machining procedure 160 is needed to bring the forged part 340 to the general form of the body 371 and/or to bring the attached part 355 to the general form of the articular surface portion 375, the machined part 360 may serve as the unfinished orthopedic device 173.

The finishing procedure 170 includes an operation 172, which generally involves receiving the finishing model 171 at the finishing device 270, and finishing the unfinished orthopedic device 173 according to the model 171. When the unfinished device 173 is substantially in the desired form for the finished device 370, the operation 172 may include performing fine material removal in order to bring the unfinished device 173 to the final form desired for the finished device 370. By way of example, such fine material removal may be performed to bring the articular surface 376 to a desired smoothness. In certain embodiments, the operation 172 may include treating one or more surfaces of the unfinished device 173. For example, in embodiments in which the orthopedic device 370 includes a porous tissue-facing region 372 intended to foster tissue in-growth, the model 171 may indicate that the operation 172 is to include treating the porous tissue-facing region 372 with a coating which promotes such tissue in-growth. As another example, the operation 172 may include plasma spraying the device 173, such as with hydroxyapatite. In certain embodiments, the operation 172 may include cleaning the unfinished device 173 to remove loose particles.

The procedure 170 may further include an operation 174, which generally involves packaging and sterilizing the finished device 370 to form a packaged unit 380. For example, the model 171 may include packaging and sterilization models, and the operation 174 may include operating the finishing device 270 to package and sterilize the finished orthopedic device 370 according to the model 171. The packaged unit 380 may then be ready for shipment and/or use.

Figure 14:
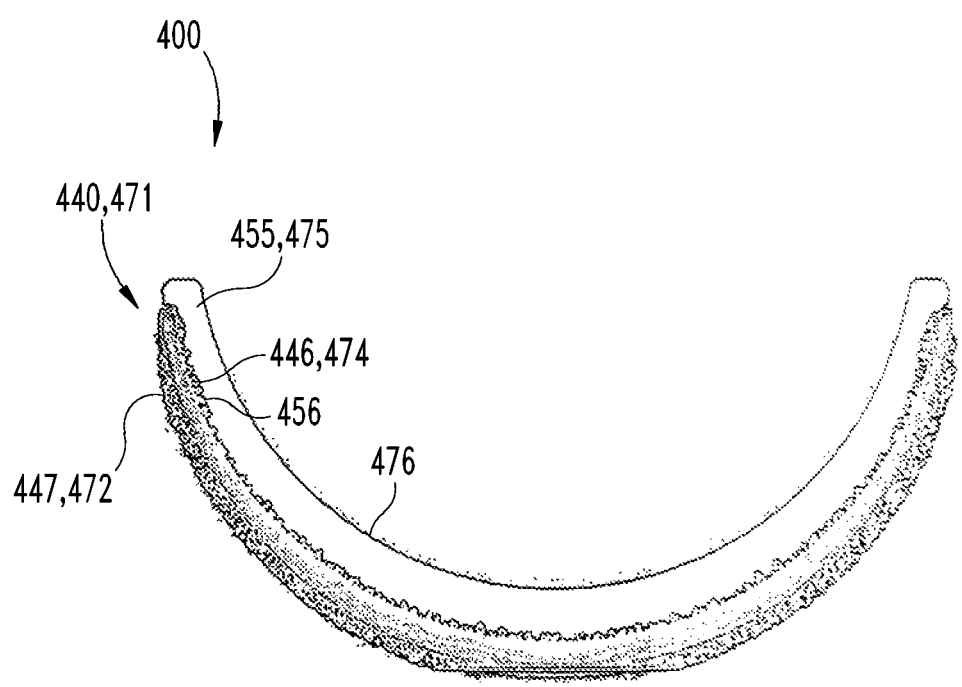
FIG. 14 is a cross-sectional illustration of an acetabular cup according to certain embodiments.

FIG. 14 illustrates an orthopedic device in the form of an acetabular cup 400 that may be created using certain embodiments of the process 100 and system 200. With continued reference to FIGS. 1-13, one exemplary implementation of the process 100 will now be described in connection with the acetabular cup 400 illustrated in FIG. 14. It is to be understood, however, that the implementation described hereinafter may be utilized to create other forms of orthopedic implants having polymeric portions, which may define an articular surface and/or a non-articular surface. By way of example, such a polymeric portion may define a non-articular surface structured to discourage attachment of soft tissue, such as muscle, tendons, and/or ligaments.

The acetabular cup 400 is an embodiment of the finished orthopedic device 370, and includes certain features which correspond to those described above in connection with the manufacturing stages illustrated in FIGS. 3-13. Unless indicated otherwise, similar reference characters are used to indicate similar elements and features. For example, the acetabular cup 400 includes a body portion 471 formed of a forged part 440 and an articular portion 475 formed of an attached part 455, which respectively correspond to the body portion 371, forged part 350, articular portion 375, and attached part 355 described above. In the interest of conciseness, the following description focuses primarily on features of the acetabular cup 400 and the instant implementation of the process 100 which may not necessarily have been described above with reference to the manufactured product 300 and the process 100.

In the instant embodiment, the body portion 471 formed of the forged part 440 includes an inward-facing fixation region 474 and a tissue-facing in-growth region 472. More specifically, the fixation region 474 is formed of the deformed layer 446, and the in-growth region 472 is formed of the second layer 447. The in-growth region 472 defines a bone-facing surface of the cup 400, and is structured to promote tissue in-growth when the cup 400 is implanted into the acetabular socket of a patient. Additionally, the fixation region 474 includes an infiltrated layer 456, through which the attached part 455 that defines the articular portion 475 is affixed to the body portion 471.

In the instant embodiment, the operation 102 includes selecting the target porosity characteristic 103 for the fixation region 474 based at least in part upon a criterion 101 relating to the molding procedure 150. For example, the criteria 101 may relate to one or more of the composition of the liquid 255, a desired infiltration of the liquid 255 into the deformed layer 346, and a desired degree of control over the infiltration. The operation 102 may include selecting the target porosity characteristic 103 to provide the desired infiltration and/or control thereof based at least in part upon the composition and/or viscosity of the liquid 255. For example, the operation 102 may include selecting the target porosity characteristic 103 with a target average pore size 103a and/or a target porosity fraction 103c sufficient to ensure that the liquid 255 does not permeate through the deformed layer 346, 446 and into the undeformed layer 347, 447. By way of example, the target porosity characteristic 103 may include a target average pore size 103a of less than 500 microns and/or a target porosity fraction 103c in the range of 15% to 35%.

In the instant embodiment, the in-growth region 472 corresponds to the undeformed layer 347 illustrated in FIG. 11, such that the in-growth region 472 has the initial porosity characteristic 107. Accordingly, the operation 106 includes selecting the initial porosity characteristic 107 based at least in part upon a criterion 105 relating to desired in-growth characteristics for the in-growth region 472. The selection of the initial porosity characteristic 107 may be further based upon at least one additional criterion 105, such as a criterion relating to desired load-bearing characteristics for the in-growth region 472. By way of example, the initial porosity characteristic 107 may include an average pore size 107a and/or porosity fraction 107c selected to promote tissue in-growth while providing the desired load bearing characteristics, such as an initial average pore size 107a of less than 1000 microns and/or a porosity fraction 107c in the range of 35% to 70%. The initial porosity characteristic 107 may additionally or alternatively include an initial pore size range 107b, such as a range 107b having a lower limit between 100 microns and 300 microns and an upper limit between 500 microns and 1000 microns.

In the modeling procedure 110, the operation 112 involves generating the porous structure model 121 with the initial porosity characteristic 107. The operation 112 may involve generating the porous structure model 121 based at least in part upon the desired final configuration of the body portion 471 of the acetabular cup 400. For example, the porous structure model 121 may have the overall configuration of the body portion 471 and a slightly greater thickness than the body portion 471, such that when the porous structure 320 is subjected to the forging procedure 140, the forged part 440 defines the body portion 471.

In the additive manufacturing procedure 120, the initial part 320 is formed according to the model 121 using a selective laser sintering additive manufacturing technique, and stresses are relieved while the initial part 320 is attached to the build plate 222. After being formed in the additive manufacturing procedure 120, the porous structure 320 is heat treated in the heat treatment procedure 130. While other times and temperatures may be utilized, in the instant embodiment, the heat treatment procedure 130 involves heating the porous structure 320 in air at 650° C. for 30 minutes.

In the forging procedure 140, the initial part 320 is heated to a desired temperature, and is struck according to the forging model 141 to form the forged part 340. In the instant embodiment, the forging procedure 140 involves striking the inner side of the initial part 320 such that the thickness 345 of the forged region 344 is between 50% and 80% of the thickness 325 of the corresponding porous portion 324 of the original part 320. As a result of the forging, the tissue-facing region 472 is defined by the undeformed layer 347, 447, and the fixation region 474 is defined by the deformed layer 346, 446. Accordingly, the tissue-facing region 472 has the initial porosity characteristic 107 selected based at least in part upon a criterion 105 related to tissue in-growth, and the fixation region 474 has the target porosity characteristic 103 selected based at least in part upon the infiltration of the liquid 255.

It is also contemplated that the forging procedure 140 may involve striking the outer side of the porous structure 320 to form a second deformed layer that defines the in-growth region 472. In such embodiments, the operation 102 may involve selecting an additional target porosity characteristic 103' for the first porous region 472 based at least in part upon a criterion 101 relating to bone in-growth, and the operation 106 may involve selecting the initial porosity characteristic 107 based at least in part upon a criterion 105 relating to the additional target porosity characteristic 103'. By way of example, the additional target porosity characteristic 103' may include a target average pore size in the range of 100 microns to 300 microns, and the initial porosity characteristic 107 may include an initial average pore size of greater than 500 microns.

Figure 15:
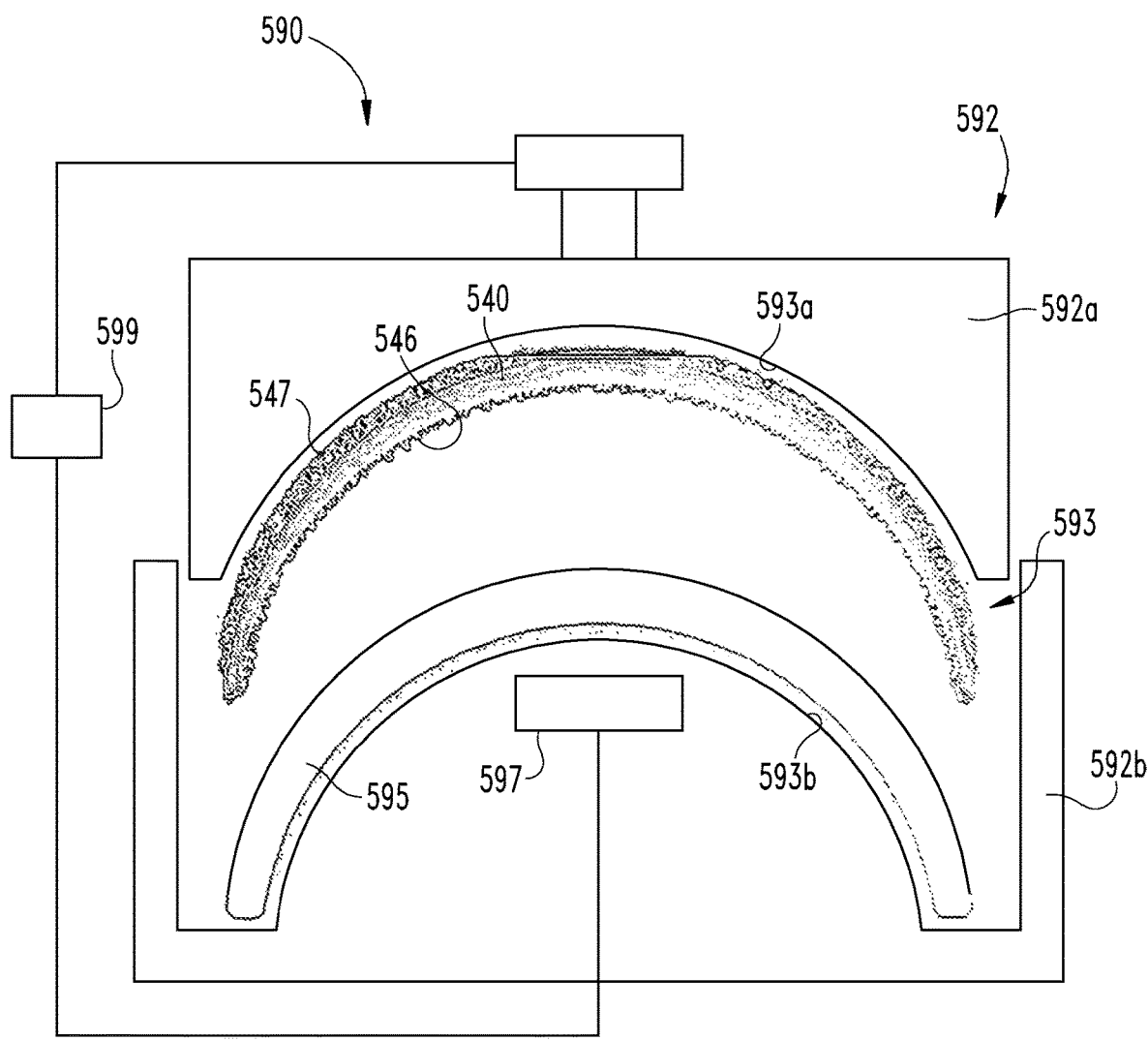
FIG. 15 is a schematic representation of a molding device being utilized in a process of creating the acetabular cup illustrated in FIG. 14.

With additional reference to FIG. 15, illustrated therein is a compression molding device 490 that may be utilized in certain forms of the molding procedure 150. The molding device 490 includes a mold 492 including first and second sections 492a, 492b, each of which includes a surface 493a, 493b that partially defines a cavity 493 of the mold 492. More specifically, the first section 492a has a first inner surface 493a which generally conforms to the outer surface of the forged part 440, and the second section 492b has a second inner surface 493b which generally conforms to the desired configuration of the articular surface 476. In the instant embodiment, the molding procedure 150 involves placing a polymeric composition 495 in the second mold section 492b such that the polymeric composition 495 generally conforms to the second inner surface 493b. With the forged part 440 seated in the first mold section 492a, an actuator 494 such as a hydraulic piston is actuated to drive first and second sections 492a, 492b toward one another, thereby causing the composition 495 to infiltrate the deformed layer 446. The composition 495 is then solidified, thereby creating the attached part 455 which defines the articular portion 475.

In certain forms, the polymeric composition 495 may be provided in the form of a partially solidified shaped charge, and the molding procedure 150 may involve solidifying the composition 495 after the deformed layer 446 is infiltrated. In other embodiments, the polymeric composition 495 may be provided in the form of a powder, and the procedure 150 may involve activating a heating element 497 to at least partially melt the composition 495, for example as the mold sections 492a, 492b are being driven together. In the event that flash is generated as a result of the compression molding, such flash may be removed in the machining procedure 160 and/or the finishing procedure 170.

With the forged part 440 defining the cup body portion 471 and the attached part 455 defining the articular portion 475, the molded part 350 may be substantially in the form of the finished acetabular cup 400. In such forms, the bulk material removal provided by the machining procedure 160 may be unnecessary, and the process 100 may continue to the finishing procedure 170 using the molded part 350 as the unfinished orthopedic device 173. In the event that bulk material removal is required, the molded part 350 may be utilized as the workpiece 163 in the machining procedure 160, and the machined part 360 may be utilized as the unfinished orthopedic device 173 in the finishing procedure 170.

With an unfinished orthopedic device 173 prepared, the process 100 may continue to the finishing procedure 170. In the finishing procedure 170, the operation 172 may include surface treating the first porous region 472 and/or the articular portion 475, for example to provide the treated components with desired wear and/or hardness characteristics. The operation 172 may additionally or alternatively include treating the first porous region 472 with a compound that promotes tissue in-growth. The finishing procedure 170 may further include packaging and/or sterilizing the acetabular cup 400, for example as described above.

Figure 16:
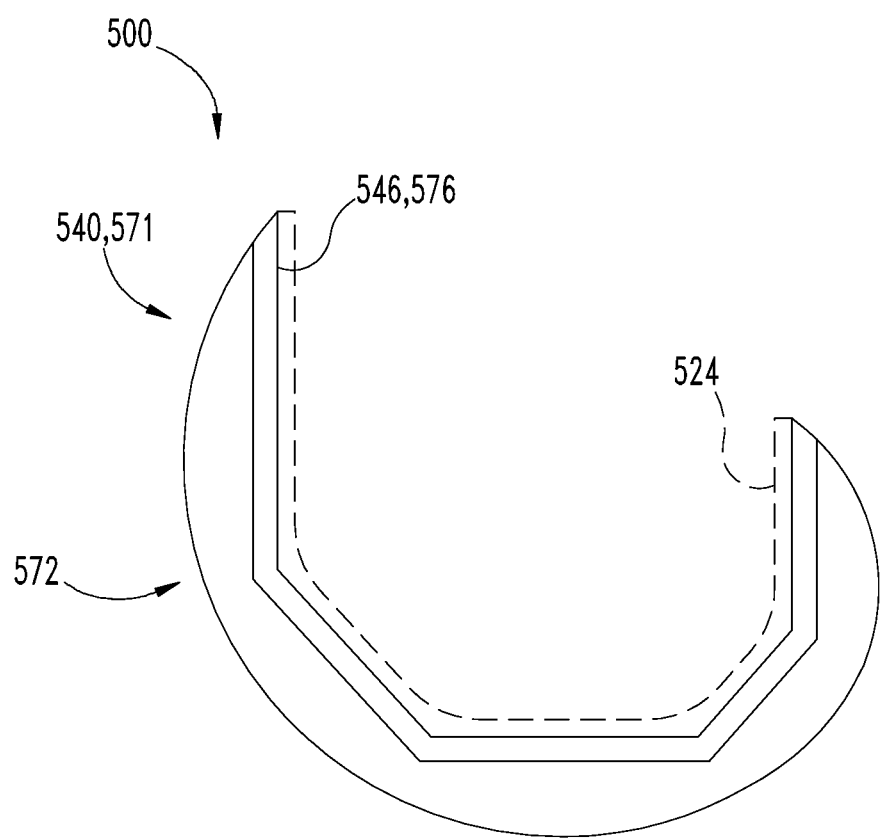
FIG. 16 is a schematic representation of a femoral implant according to certain embodiments.

FIG. 16 illustrates an orthopedic device in the form of a femoral implant 500 that may be created using certain embodiments of the process 100 and system 200. With continued reference to FIGS. 1-13, another exemplary implementation of the process 100 will now be described in connection with the femoral implant 500 illustrated in FIG. 16. It is to be understood, however, that the implementation described hereinafter may be utilized to create other forms of orthopedic devices and instruments, such as tibial or patellar implants.

The femoral implant 500 is an embodiment of the finished orthopedic device 370, and includes certain features that correspond to those described above in connection with the manufacturing stages illustrated in FIGS. 3-13. Unless indicated otherwise, similar reference characters are used to indicate similar elements and features. For example, the femoral implant 500 includes a body portion 571 formed of a forged part 540 having a deformed layer 546 defining an in-growth region 576, which respectively correspond to the body portion 371, forged part 340, deformed layer 346, and tissue-facing region 376 described above. In the interest of conciseness, the following description focuses primarily on features of the femoral implant 500 and the instant implementation of the process 100 that may not necessarily have been described above with reference to the manufactured product 300 and the process 100.

The operation 102 involves selecting the target porosity characteristic 103 based at least in part upon a criterion 101 relating to desired in-growth characteristics for the in-growth region 576. The selection of the target porosity characteristic 103 may be further based upon at least one additional criterion 101, such as a criterion relating to desired load-bearing characteristics for the in-growth region 576. By way of example, the target porosity characteristic 103 may include an average pore size and/or porosity selected to promote tissue in-growth while providing the desired load bearing characteristics, such as an initial average pore size 107a of less than 1000 microns and/or a porosity fraction 107c in the range of 35% to 70%. The target porosity characteristic 103 may additionally or alternatively include an initial pore size range 103b, such as a range 103b having a lower limit between 100 microns and 300 microns and an upper limit between 500 microns and 1000 microns.

The operation 106 involves selecting an initial porosity characteristic 107 greater than the target porosity characteristic 103. More specifically, the operation 106 involves selecting the initial porosity characteristic based at least in part upon a criterion 105 relating to at least one of the modeling procedure 110 and the additive manufacturing procedure 120. By way of example, the criterion 105 may relate to computing time associated with the generation of the porous structure model 121 in the operation 112 and/or build time associated with manufacturing the initial part 320 in the operation 122, and the operation 106 may involve selecting the initial porosity characteristic 107 to reduce or optimize the computing time and/or build time. The initial porosity characteristic 107 may include one or more of a target average pore size 107a greater than 1000 microns, a pore size range 107b having a minimum pore size in the range of 800 microns to 1200 microns, and/or a porosity fraction 107c in the range of 50% to 85%. In the instant implementation, the initial porosity characteristic 107 includes a pore size range 107b having a minimum pore size greater than that which is desired for tissue in-growth, such as a minimum pore size of 1000 microns.

In the additive manufacturing procedure 120, the initial part 320 is manufactured with a porous portion 524 having initial pores 329 larger than the minimum pore size of 1000 microns. The initial part 320 is then forged in the forging procedure 140, thereby forming the in-growth region 576 with the target porosity characteristic 103. In certain embodiments, the forging procedure 140 may include striking the porous portion 324, 524 such that the sizes of at least a predetermined percentage of the pores in the in-growth region 576 are less than the upper limit of the target range 103b. By way of example, the forging procedure 140 may result in at least 90% of the pores in the in-growth region 576 having a pore size less than an upper limit of 1000 microns. The forged part 540 may then be subjected to the machining procedure 160 and/or the finishing procedure 170 to produce the finished femoral implant 500.

In the illustrated embodiment, the articular portion 572 of the femoral implant is formed during the additive manufacturing procedure 120, such that the articular portion 572 is included in the initial part 320. In other embodiments, the articular portion 572 may not necessarily be included in the initial part 320. As one example, the articular portion 572 may be formed by infiltrating a forged part with a polymeric composition, for example as described above with reference to FIGS. 10 and 11 and/or FIG. 14. In other embodiments, the articular portion 572 may be a metal part formed according to known techniques. In such forms, the forged part 540 may define the in-growth region 576, and the in-growth region 576 may be attached to the articular portion 572 using known techniques, such as sintering are diffusion bonding.

Figure 17:
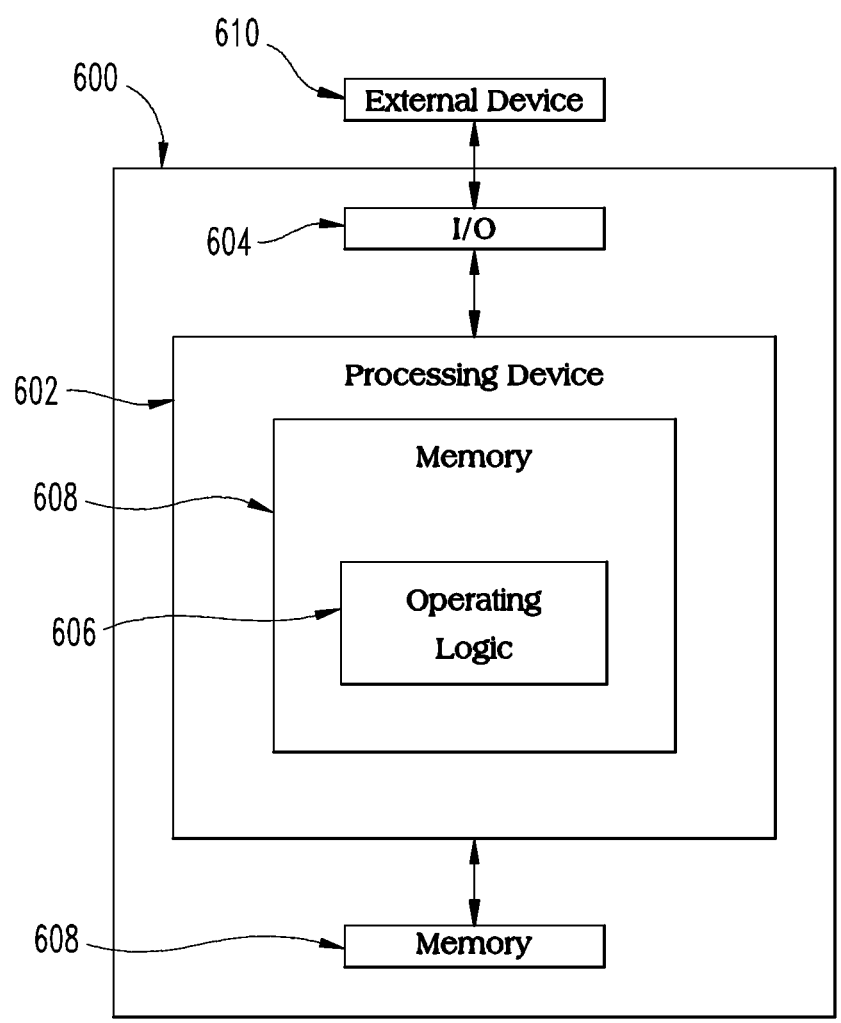
FIG. 17 is a schematic block diagram of a computing device which may be utilized in connection with certain embodiments.

FIG. 17 is a schematic block diagram of a computing device 600. The computing device 600 is one example of a computer, server, mobile device, reader device, or equipment configuration which may be utilized in connection with the system 200 illustrated in FIG. 2. The computing device 600 includes a processing device 602, an input/output device 604, memory 606, and operating logic 608. Furthermore, the computing device 600 communicates with one or more external devices 610.

The input/output device 604 allows the computing device 600 to communicate with the external device 610. For example, the input/output device 604 may be a network adapter, network card, interface, or a port (e.g., a USB port, serial port, parallel port, an analog port, a digital port, VGA, DVI, HDMI, FireWire, CAT 5, or any other type of port or interface). The input/output device 604 may be comprised of hardware, software, and/or firmware. It is also contemplated that the input/output device 604 may include more than one of these adapters, cards, or ports.

The external device 610 may be any type of device that allows data to be inputted or outputted from the computing device 600. For example, the external device 610 may be a mobile device, a reader device, equipment, a handheld computer, a diagnostic tool, a controller, a computer, a server, a printer, a display, an alarm, an illuminated indicator such as a status indicator, a keyboard, a mouse, or a touch screen display. Furthermore, it is contemplated that the external device 610 may be integrated into the computing device 600. It is further contemplated that there may be more than one external device in communication with the computing device 600.

The processing device 602 can be of a programmable type, a dedicated, hardwired state machine, or a combination of these; and can further include multiple processors, Arithmetic-Logic Units (ALUs), Central Processing Units (CPUs), Digital Signal Processors (DSPs) or the like. For forms of processing device 602 with multiple processing units, distributed, pipelined, and/or parallel processing can be utilized as appropriate. The processing device 602 may be dedicated to performance of just the operations described herein or may be utilized in one or more additional applications. In the depicted form, the processing device 602 is of a programmable variety that executes algorithms and processes data in accordance with operating logic 608 as defined by programming instructions (such as software or firmware) stored in memory 606. Alternatively or additionally, the operating logic 608 for processing device 602 is at least partially defined by hardwired logic or other hardware. The processing device 602 can be comprised of one or more components of any type suitable to process the signals received from input/output device 604 or elsewhere, and provide desired output signals. Such components may include digital circuitry, analog circuitry, or a combination of both.

The memory 606 may be of one or more types, such as a solid-state variety, electromagnetic variety, optical variety, or a combination of these forms. Furthermore, the memory 606 can be volatile, nonvolatile, or a combination of these types, and some or all of memory 606 can be of a portable variety, such as a disk, tape, memory stick, cartridge, or the like. In addition, the memory 606 can store data that is manipulated by the operating logic 608 of the processing device 602, such as data representative of signals received from and/or sent to the input/output device 604 in addition to or in lieu of storing programming instructions defining the operating logic 608, just to name one example. As shown in FIG. 6, the memory 606 may be included with the processing device 602 and/or coupled to the processing device 602.

The processes in the present application may be implemented in the operating logic 608 as operations by software, hardware, artificial intelligence, fuzzy logic, or any combination thereof, or at least partially performed by a user or operator. In certain embodiments, units represent software elements as a computer program encoded on a non-transitory computer readable medium, wherein one or more of the controllers illustrated in connection with the system 200 performs the described operations when executing the computer program.

Certain embodiments of the present disclosure relate to a method comprising: selecting a target porosity characteristic for a porous region of an orthopedic device based at least in part upon a desired performance characteristic for the porous region; selecting an initial porosity characteristic based at least in part upon the target porosity characteristic, wherein the initial porosity characteristic is greater than the target porosity characteristic; manufacturing an initial part using an additive manufacturing procedure, wherein the initial part includes a porous portion having the initial porosity characteristic; forming a deformed part from the initial part, wherein forming the deformed part includes mechanically deforming at least a portion of the initial part to form a deformed layer having the target porosity characteristic; and forming the orthopedic device from the deformed part, wherein forming the orthopedic device from the deformed part includes forming the porous region from the deformed layer of the deformed part.

In certain embodiments, forming the deformed part includes mechanically deforming at least a portion of the initial part using at least one of forging, rolling, and deep-drawing.

In certain embodiments, forming the deformed part includes mechanically deforming at least a portion of the initial part by striking the porous portion.

In certain embodiments, the additive manufacturing process includes building the initial part on a build plate, and the method further comprises relieving stresses in the initial part with the initial part attached to the build plate.

In certain embodiments, building the initial part on the build plate includes forming a plurality of layers, forming each layer includes scanning a beam along a bed of powdered raw material to form a melt pool and solidifying the melt pool, and the method further comprises removing the initial part from the build plate after relieving stresses from the initial part, and cleaning the initial part to remove loose powder from the initial part prior to forging the initial part.

In certain embodiments, the orthopedic device is an unfinished orthopedic device, and the method further comprises finishing the unfinished orthopedic device, thereby forming a finished orthopedic device.

In certain embodiments, the forming the unfinished orthopedic device from the deformed part comprises a molding procedure; the molding procedure comprises placing at least the deformed layer in a mold, infiltrating the deformed layer with a polymeric composition to form an infiltrated layer within the deformed layer, and solidifying the polymeric composition to form an attached part; and the attached part is attached to the deformed part by the solidified polymeric composition within the infiltrated layer.

In certain embodiments, the polymeric composition comprises a liquid polymeric composition, the attached part includes a smooth surface, the mold has an internal surface corresponding to the smooth surface, the molding procedure comprises an injection molding procedure, and infiltrating the deformed layer includes injecting the liquid polymeric composition into the mold.

In certain embodiments, the attached part includes a smooth surface, the mold has an internal surface corresponding to the smooth surface, the molding procedure comprises a compression molding procedure which further includes placing the polymeric composition adjacent the internal surface, and infiltrating the deformed region includes driving the deformed layer toward the internal surface of the mold.

Certain embodiments of the present disclosure relate to a method comprising: manufacturing an initial part using an additive manufacturing procedure, wherein the initial part includes a first porous portion having an initial porosity characteristic; forging the initial part to form a forged part, wherein the forging includes striking an external surface of the initial part to form a forged region from the first porous portion, and wherein the forged region includes a deformed layer having a target porosity characteristic lower than the initial porosity characteristic; forming an unfinished orthopedic device from the forged part; and forming a finished orthopedic device from the unfinished orthopedic device, the finished orthopedic device including a porous region formed of the deformed layer.

In certain embodiments, the method further comprises selecting the target porosity characteristic based at least in part upon a first criterion, and selecting the initial porosity characteristic based at least in part upon the target porosity characteristic and a second criterion.

In certain embodiments, the first criterion relates to a desired characteristic of the deformed layer, and the second criterion relates to the additive manufacturing procedure.

In certain embodiments, the target porosity characteristic includes a target pore size, the initial porosity characteristic includes an initial pore size, the second criterion relates to a threshold pore size for the additive manufacturing procedure, and selecting the initial porosity characteristic based upon the target porosity characteristic and the second criterion includes selecting the initial pore size greater than each of the target pore size and the threshold pore size.

In certain embodiments, the target pore size includes an average target pore size, and the initial pore size includes an average initial pore size.

In certain embodiments, the additive manufacturing procedure includes melting a powder having a powder diameter to form a melt pool having a melt pool diameter, and the threshold pore size corresponds to at least one of the powder diameter and the melt pool diameter.

In certain embodiments, the target average pore size is less than the threshold pore size, and the initial average pore size is greater than the threshold pore size.

In certain embodiments, the forged region further includes a second layer formed from the first porous portion, the second layer having a greater porosity than the deformed layer.

In certain embodiments, forming the unfinished orthopedic device from the forged part comprises forming a molded part from the forged part and forming the unfinished orthopedic device from the molded part, the molded part includes the forged part and an attached part, forming the molded part includes infiltrating a polymeric composition into the deformed layer and solidifying the liquid to form the attached part.

In certain embodiments, the first criterion relates to infiltration of the polymeric composition into the deformed layer, and selecting the target porosity characteristic includes selecting the target porosity characteristic to discourage the polymeric composition from passing through the deformed layer into the second layer.

In certain embodiments, the finished orthopedic device includes a tissue-facing surface defined by the second layer, the second layer has the initial porosity characteristic, and the second criterion relates to tissue in-growth within the second layer.

In certain embodiments, the method further comprises generating a porous structure model having the selected initial porosity characteristic, and the additive manufacturing procedure includes building at least the first portion of the initial part according to the porous structure model.

Certain embodiments of the present disclosure relate to a method of creating an orthopedic device, the method comprising: manufacturing an initial part using an additive manufacturing procedure, wherein the initial part has a first outer surface and a second outer surface, wherein the initial part comprises a porous portion including a first layer defining the outer surface, a second layer defining the second outer surface, and a plurality of pores having an initial average pore size; forming a forged part from the initial part, wherein forming the forged part includes forging the porous portion to form a forged region, wherein forging the porous portion includes deforming the first layer by striking the first outer surface, thereby deforming the pores in the first layer, wherein the deformed first layer has a first layer average pore size less than the initial average pore size, and wherein the second layer has a second layer average pore size greater than the first layer average pore size; forming an orthopedic device from the forged part, the orthopedic device including a tissue-facing region formed of one of the first and second layers, wherein the tissue-facing region has a tissue in-growth average pore size selected to promote in-growth of tissue in the tissue-facing region, and wherein the average pore size of the one of the first and second layers corresponds to the tissue in-growth average pore size.

In certain embodiments, the method further comprises selecting a target average pore size based at least in part upon a first criterion, and selecting the initial average pore size based at least in part upon a second criterion, wherein selecting the initial pore size includes selecting the initial pore size greater than the target average pore size, and wherein one of the first criterion and the second criterion relates to tissue in-growth, and wherein the first layer average pore size corresponds to the target average pore size.

In certain embodiments, the tissue-facing region is formed of the first layer, the first criterion relates to tissue in-growth, and the second criterion relates to the additive manufacturing procedure.

In certain embodiments, the first layer average pore size is less than 1000 microns, and the initial average pore size is greater than 1000 microns.

In certain embodiments, the tissue-facing region is formed of the second layer, forming the orthopedic device from the forged part includes forming an attached part of the orthopedic device by infiltrating a liquid into the deformed first layer and solidifying the liquid, the first criterion relates to infiltration of the liquid, and the second criterion relates to tissue in-growth.

In certain embodiments, the target average pore size is less than 500 microns, and the initial average pore size is less than 1000 microns.

While the invention has been illustrated and described in detail in the drawings and foregoing description, the same is to be considered as illustrative and not restrictive in character, it being understood that only the preferred embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. A method, comprising:
   selecting a target porosity characteristic for a porous region of an orthopedic device based at least in part upon a desired performance characteristic for the porous region;
   selecting an initial porosity characteristic based at least in part upon the target porosity characteristic, wherein the initial porosity characteristic corresponds to a greater porosity than the target porosity characteristic;
   manufacturing an initial part including a porous portion having the initial porosity characteristic; and
   manufacturing a deformed part from the initial part, wherein manufacturing the deformed part includes mechanically deforming at least a portion of the initial part to form a deformed layer having the target porosity characteristic.

2. The method of claim 1, wherein the manufacturing of the initial part comprises using an additive manufacturing procedure, the additive manufacturing process includes building the initial part on a build plate; and
   wherein the method further comprises relieving stresses in the initial part with the initial part attached to the build plate.

3. The method of claim 2, wherein building the initial part on the build plate includes successively forming a plurality of layers;
   wherein forming each layer includes scanning a beam along a bed of powdered raw material to form a melt pool and solidifying the melt pool; and
   wherein the method further comprises:
      removing the initial part from the build plate after relieving stresses from the initial part; and
      cleaning the initial part to remove loose powder from the initial part prior to the mechanically deforming.

4. The method of claim 1, further comprising forming the orthopedic device from the deformed part, wherein forming the orthopedic device from the deformed part includes forming the porous region from the deformed layer of the deformed part.

5. The method of claim 4, wherein the orthopedic device is an unfinished orthopedic device; and
   wherein the method further comprises performing a finishing procedure on the unfinished orthopedic device, thereby forming a finished orthopedic device.

6. The method of claim 5, wherein the forming of the unfinished orthopedic device from the deformed part comprises a molding procedure;
   wherein the molding procedure comprises placing at least the deformed layer in a mold, infiltrating the deformed layer with a polymeric composition to form an infiltrated layer within the deformed layer, and solidifying the polymeric composition to form an attached part; and
   wherein the attached part is attached to the deformed part by the solidified polymeric composition within the infiltrated layer.

7. The method of claim 6, wherein the polymeric composition comprises a liquid polymeric composition;
wherein the attached part includes a smooth surface;
wherein the mold has an internal surface corresponding to the smooth surface;
wherein the molding procedure comprises an injection molding procedure; and
wherein infiltrating the deformed layer includes injecting the liquid polymeric composition into the mold.

8. The method of claim 6, wherein the attached part includes a smooth surface;
wherein the mold has an internal surface corresponding to the smooth surface;
wherein the molding procedure comprises a compression molding procedure which further includes placing the polymeric composition adjacent the internal surface; and
wherein infiltrating the deformed region includes driving the deformed layer toward the internal surface of the mold.

9. A method, comprising:
manufacturing an initial part including a first porous portion having an initial porosity characteristic;
forging the initial part to form a forged part, wherein the forging includes striking an external surface of the initial part to form a forged region from the first porous portion, and wherein the forged region includes a deformed layer having a target porosity characteristic lower than the initial porosity characteristic; and
forming an orthopedic device from the forged part.

10. The method of claim 9, further comprising selecting the target porosity characteristic based at least in part upon a first criterion, and selecting the initial porosity characteristic based at least in part upon the target porosity characteristic and a second criterion.

11. The method of claim 10, wherein the first criterion relates to a desired characteristic of the deformed layer;
wherein the target porosity characteristic includes a target pore size;
wherein the initial porosity characteristic includes an initial pore size;
wherein the second criterion relates to a threshold pore size; and
wherein selecting the initial porosity characteristic based upon the target porosity characteristic and the second criterion includes selecting the initial pore size greater than each of the target pore size and the threshold pore size.

12. The method of claim 11, wherein the manufacturing of the initial part comprises using an additive manufacturing procedure;
wherein the additive manufacturing procedure includes melting a powder having a powder diameter to form a melt pool having a melt pool diameter;
wherein the threshold pore size corresponds to at least one of the powder diameter and the melt pool diameter;
wherein the target average pore size is less than the threshold pore size; and
wherein the initial average pore size is greater than the threshold pore size.

13. The method of claim 9, wherein the manufacturing of the initial part comprises using an additive manufacturing procedure.

14. The method of claim 9, wherein the forged region further includes a second layer formed from the first porous portion, the second layer having a greater porosity than the deformed layer;
wherein forming the orthopedic device from the forged part comprises forming a molded part from the forged part and forming the orthopedic device from the molded part;
wherein the molded part includes the forged part and an attached part; and
wherein forming the molded part includes infiltrating a polymeric composition into the deformed layer and solidifying the liquid to form the attached part.

15. The method of claim 9, further comprising finishing the orthopedic device, the finished orthopedic device including a porous region formed of the deformed layer;
wherein the finished orthopedic device includes a tissue-facing surface defined by a second layer formed from the first porous portion, the second layer having a greater porosity than the deformed layer; and
wherein the second layer has the initial porosity characteristic.

16. A method of creating an orthopedic device, the method comprising:
manufacturing an initial part having a first outer surface and a second outer surface, wherein the initial part comprises a porous portion including a first layer defining the first outer surface, a second layer defining the second outer surface, and a plurality of pores having an initial average pore size; and
forming a forged part from the initial part, wherein forming the forged part includes forging the porous portion to form a forged region, wherein forging the porous portion includes deforming the first layer by striking the first outer surface, thereby deforming the pores in the first layer, wherein the deformed first layer has a first layer average pore size less than the initial average pore size, and wherein the second layer has a second layer average pore size greater than the first layer average pore size.

17. The method of claim 16, further comprising selecting a target average pore size based at least in part upon a first criterion, and selecting the initial average pore size based at least in part upon a second criterion;
wherein selecting the initial average pore size includes selecting the initial average pore size greater than the target average pore size;
wherein one of the first criterion and the second criterion relates to tissue in-growth; and
wherein the first layer average pore size corresponds to the target average pore size.

18. The method of claim 16, further comprising forming an orthopedic device from the forged part, the orthopedic device including a tissue-facing region formed of one of the first and second layers, wherein the tissue-facing region has a tissue in-growth average pore size selected to promote in-growth of tissue in the tissue-facing region, and wherein the average pore size of the one of the first and second layers corresponds to the tissue in-growth average pore size.

19. The method of claim 16, wherein manufacturing the initial part comprises using an additive manufacturing procedure.

* * * * *